United States Patent
Muratore et al.

(10) Patent No.: US 12,275,735 B2
(45) Date of Patent: Apr. 15, 2025

(54) ERGOLINE ANALOGUES

(71) Applicant: BECKLEY PSYTECH LIMITED, Oxford (GB)

(72) Inventors: Massimo Muratore, Oxford (GB); Amir Lotfi Moghaddam, Oxford (GB); Christopher Wong, Oxford (GB)

(73) Assignee: Beckley Psytech Limited, Oxford (GB)

(*) Notice: Subject to any disclaimer, the term of this patent is extended or adjusted under 35 U.S.C. 154(b) by 0 days.

(21) Appl. No.: 18/462,899

(22) Filed: Sep. 7, 2023

(65) Prior Publication Data

US 2024/0116936 A1 Apr. 11, 2024

Related U.S. Application Data

(63) Continuation of application No. 17/932,854, filed on Sep. 16, 2022, now Pat. No. 11,787,806, which is a continuation of application No. 17/941,506, filed on Sep. 9, 2022, now Pat. No. 11,697,651, which is a continuation of application No. PCT/IB2022/050355, filed on Jan. 17, 2022.

(30) Foreign Application Priority Data

| Jan. 15, 2021 | (GB) | 2100549 |
| May 18, 2021 | (GB) | 2107104 |
| Nov. 11, 2021 | (GB) | 2116270 |

(51) Int. Cl.
- *C07D 471/06* (2006.01)
- *A61K 9/00* (2006.01)
- *A61K 9/20* (2006.01)
- *C07D 519/00* (2006.01)

(52) U.S. Cl.
CPC ........ *C07D 471/06* (2013.01); *A61K 9/0019* (2013.01); *A61K 9/0031* (2013.01); *A61K 9/0056* (2013.01); *A61K 9/006* (2013.01); *A61K 9/0073* (2013.01); *A61K 9/2072* (2013.01); *C07D 519/00* (2013.01)

(58) Field of Classification Search
CPC .. C07D 471/06; C07D 519/00; A61K 9/0019; A61K 9/0031; A61K 9/0056; A61K 9/006; A61K 9/0073; A61K 9/2072
USPC ......................................................... 546/26
See application file for complete search history.

(56) References Cited

U.S. PATENT DOCUMENTS

| 2,774,763 | A | 12/1956 | Garbrecht |
| 2,997,470 | A | 8/1961 | Pioch |
| 3,224,945 | A | 12/1965 | Tyler, Jr. |
| 4,176,182 | A | 11/1979 | Ferrari et al. |

(Continued)

FOREIGN PATENT DOCUMENTS

| CH | 578565 A5 | 8/1976 |
| CN | 103816150 A | 5/2014 |

(Continued)

OTHER PUBLICATIONS

Gupta, S. P., "QSAR studies on drugs acting at the central nervous system," Chemical Reviews, vol. 89, No. 8, pp. 1765-1800 (1989).

(Continued)

*Primary Examiner* — Taylor V Oh
(74) *Attorney, Agent, or Firm* — Clark & Elbing LLP

(57) ABSTRACT

This invention relates to pharmaceutically acceptable ergoline analogues and salts thereof. In particular, though not exclusively, the invention relates to formulations and uses of the same as a medicament.

20 Claims, 5 Drawing Sheets

(56) References Cited

U.S. PATENT DOCUMENTS

| | | |
|---|---|---|
| 4,180,581 A | 12/1979 | Stadler |
| 4,348,391 A | 9/1982 | Stutz et al. |
| 10,519,175 B2 | 12/2019 | Londesbrough et al. |
| 2008/0293695 A1 | 11/2008 | Bristol et al. |
| 2009/0264456 A1 | 10/2009 | Sewell |
| 2012/0108510 A1 | 5/2012 | Young et al. |
| 2017/0348303 A1 | 12/2017 | Bosse et al. |
| 2017/0360772 A1 | 12/2017 | Bosse et al. |
| 2018/0147142 A1 | 5/2018 | Knight |
| 2020/0046687 A1 | 2/2020 | Apkarian |
| 2020/0179349 A1 | 6/2020 | Yun et al. |
| 2020/0187777 A1 | 6/2020 | Luderer et al. |
| 2021/0058956 A1 | 2/2021 | Chatterjee et al. |
| 2021/0322743 A1 | 10/2021 | Rinti et al. |
| 2022/0362237 A1 | 11/2022 | Barrow et al. |

FOREIGN PATENT DOCUMENTS

| | | |
|---|---|---|
| CN | 113288883 A | 8/2021 |
| DE | 2617738 A1 | 11/1976 |
| EP | 0008802 A1 | 3/1980 |
| EP | 0026899 A1 | 4/1981 |
| EP | 0131301 A2 | 1/1985 |
| EP | 2067780 A1 | 6/2009 |
| EP | 3868364 A1 | 8/2021 |
| EP | 4159192 A1 | 4/2023 |
| EP | 4159201 A1 | 4/2023 |
| GB | 912715 A | 12/1962 |
| GB | 1410349 A | 10/1975 |
| GB | 1584464 A | 2/1981 |
| GB | 2588505 A | 4/2021 |
| WO | WO-02/38142 A2 | 5/2002 |
| WO | WO-2010/054202 A2 | 5/2010 |
| WO | WO-2013191704 A1 | 12/2013 |
| WO | WO-2016118541 A1 | 7/2016 |
| WO | WO-2016/145193 A1 | 9/2016 |
| WO | WO-2018064465 A1 | 4/2018 |
| WO | WO-2018/195455 A1 | 10/2018 |
| WO | WO-2019/073379 A1 | 4/2019 |
| WO | WO-2019/081764 A1 | 5/2019 |
| WO | WO-2019/246532 A1 | 12/2019 |
| WO | WO-2020/157569 A1 | 8/2020 |
| WO | WO-2020/169851 A1 | 8/2020 |
| WO | WO-2020/176597 A1 | 9/2020 |
| WO | WO-2020/181194 A1 | 9/2020 |
| WO | WO-2020/212948 A1 | 10/2020 |
| WO | WO-2020/212951 A1 | 10/2020 |
| WO | WO-2021/003467 A1 | 1/2021 |
| WO | WO-2021/019023 A1 | 2/2021 |
| WO | WO-2021030571 A1 | 2/2021 |
| WO | WO-2021076572 A1 | 4/2021 |
| WO | WO-2021/089872 A1 | 5/2021 |
| WO | WO-2021155470 A1 | 8/2021 |
| WO | WO-2021175816 A1 | 9/2021 |
| WO | WO-2021179091 A1 | 9/2021 |
| WO | WO-2021/209815 A1 | 10/2021 |
| WO | WO-2021/222885 A1 | 11/2021 |
| WO | WO-2021/225796 A1 | 11/2021 |
| WO | WO-2021/250434 A1 | 12/2021 |
| WO | WO-2021253116 A1 | 12/2021 |
| WO | WO-2022000091 A1 | 1/2022 |
| WO | WO-2022008627 A2 | 1/2022 |
| WO | WO-2022016289 A1 | 1/2022 |
| WO | WO-2022038299 A1 | 2/2022 |
| WO | WO-2022094719 A1 | 5/2022 |
| WO | WO-2022125616 A1 | 6/2022 |
| WO | WO-2022133314 A1 | 6/2022 |
| WO | WO-2022153266 A1 | 7/2022 |
| WO | WO-2022153268 A1 | 7/2022 |
| WO | WO-2022175821 A1 | 8/2022 |
| WO | WO-2022207746 A1 | 10/2022 |
| WO | WO-2022246572 A1 | 12/2022 |
| WO | WO-2023002005 A1 | 1/2023 |
| WO | WO-2023028086 A1 | 3/2023 |
| WO | WO-2023186797 A1 | 10/2023 |
| WO | WO-2023186798 A1 | 10/2023 |
| WO | WO-2023186806 A1 | 10/2023 |
| WO | WO-2023186808 A1 | 10/2023 |
| WO | WO-2023186816 A1 | 10/2023 |
| WO | WO-2023186820 A1 | 10/2023 |
| WO | WO-2023186821 A1 | 10/2023 |
| WO | WO-2023186823 A1 | 10/2023 |
| WO | WO-2023186824 A1 | 10/2023 |
| WO | WO-2023186826 A1 | 10/2023 |
| WO | WO-2023186827 A1 | 10/2023 |
| WO | WO-2023186828 A1 | 10/2023 |
| WO | WO-2023186829 A1 | 10/2023 |
| WO | WO-2023186830 A1 | 10/2023 |
| WO | WO-2023186831 A1 | 10/2023 |
| WO | WO-2023186832 A1 | 10/2023 |
| WO | WO-2023186834 A1 | 10/2023 |
| WO | WO-2023186835 A1 | 10/2023 |
| WO | WO-2023186837 A1 | 10/2023 |
| WO | WO-2024146917 A1 | 7/2024 |
| WO | WO-2024160389 A1 | 8/2024 |
| WO | WO-2024160390 A1 | 8/2024 |
| WO | WO-2024160391 A1 | 8/2024 |
| WO | WO-2024160392 A1 | 8/2024 |

OTHER PUBLICATIONS

Stoll, A. et al., "Amide der stereoisomeren Lysergsäuren und Dihydro-lysergsauren. 38. Mitteilung über Mutterkornalkaloide," Helvetica Chimica Acta., vol. 38, No. 3, pp. 421-433 (1955).

Johnson, F. et al., "Emetic activity of reduced lysergamides," Journal of Medicinal Chemistry, vol. 16, No. 5, pp. 532-537 (1973).

Halberstadt A. L. et al., "Pharmacological characterization of the LSD analog N-ethyl-N-cyclopropyl lysergamide (ECPLA)," Psychopharmacology, vol. 236, pp. 799-808 (2019).

Huang X et al., "Drug discrimination and receptor binding studies of N-isopropyl lysergamide derivatives," Pharmacology Biochemistry and Behavior, vol. 47, No. 3, pp. 667-673 (1994).

Glässer, "Some Pharmacological Actions of D-Lysergic Acid Methyl Carbinolamide," Nature, vol. 189, pp. 313-314 (1961).

International Search Report and Written Opinion dated Jun. 13, 2022, in corresponding International Application No. PCT/IB2022/050355 (20 pages).

Ishii et al., "Studies on lysergic acid diethylamide and related compounds. Part 8. Structural identification of new metabolites of lysergic acid diethylamide obtained by microbial transformation using *Streptomyces roseochromogenes*," J Chem Soc Perkin 1. 4:902-5 (1980).

Ishii et al., "Studies on Lysergic Acid Diethylamide and Related Compounds. IX. Microbial Transformation of Amides Related to Lysergic Acid Diethylamide by *Streptomyces roseochromogenes*," Chem Pharm Bull. 27(12):3029-38 (1979).

Nakahara et al., "Studies on lysergic acid diethylamide and related compounds. 3. Improvement of amidation of lysergic acid," Yakugaku Zasshi. 94(3):407-12 (Mar. 1974). English abstract included.

"Beckley Psytech and PsyPAN launch Participant Impact Report and Peer Support Pilot Program," Beckley Psytech Press Release Jun. 14, 2024 (7 pages).

"Beckley Psytech Announces Dosing of First Healthy Volunteers in Phase 1 Clinical Trial Assessing Safety and Pharmacokinetics of Second Innovative Formulation of 5-MeO-DMT," Apr. 5, 2022. https://www.businesswire.com/news/home/20220404005960/en/Beckley-Psytech-Announces-Dosing-of-First-Healthy-Volunteers-in-Phase-1-Clinical-Trial-Assessing-Safety-and-Pharmacokinetics-of-Second-Innovative-Formulation-of-5-MeO-DMT. (2 pages).

"Beckley Psytech Announces First Cohort Dosed in Phase 1 Clinical Trial Assessing Safety and Tolerability of Intranasal 5-MeO-DMT," Oct. 25, 2021. https://www.businesswire.com/news/home/20211024005026/en/Beckley-Psytech-Announces-First-Cohort-Dosed-in-Phase-1-Clinical-Trial-Assessing-Safety-and-Tolerability-of-Intranasal-5-MeO-DMT. (2 pages).

"Beckley Psytech Announces First Cohort of Psychotherapists Have Begun Training for Treatment Resistant Depression Phase 2 Trials," Jan. 24, 2022. https://www.businesswire.com/news/home/20220123005101/en/Beckley-Psytech-Announces-First-Cohort-of-

(56) References Cited

OTHER PUBLICATIONS

Psychotherapists-Have-Begun-Training-for-Treatment-Resistant-Depression-Phase-2-Trials. (3 pages).
"Beckley Psytech Announces First Participant Dosed in Phase I Trial of ELE-101, A Novel Intravenous Formulation of Psilocin," Nov. 9, 2022. https://www.businesswire.com/news/home/20221108005986/en/Beckley-Psytech-Announces-First-Participant-Dosed-in-Phase-I-Trial-of-ELE-101-A-Novel-Intravenous-Formulation-of-Psilocin. (2 pages).
"Beckley Psytech announces first patient has received low-dose psilocybin in world-first clinical trial for rare headache disorder," Beckley Psytech Press Release Sep. 14, 2021 (5 pages).
"Beckley Psytech announces initial results from Phase I study and first patients dosed in Phase IIa study of ELE-101 (IV psilocin benzoate) for Major Depressive Disorder," Beckley Psytech Press Release Jun. 20, 2024 (7 pages).
"Beckley Psytech Announces Partnership With Empatica in Latest Step of Digital Strategy, Designed to Deliver Personalised Patient Care," May 19, 2022. https://www.businesswire.com/news/home/20220518006041/en/Beckley-Psytech-Announces-Partnership-With-Empatica-in-Latest-Step-of-Digital-Strategy-Designed-to-Deliver-Personalised-Patient-Care. (4 pages).
"Beckley Psytech Announces Partnership With Ksana Health, Building on Digital Strategy to Deliver Optimised Patient Outcomes," Jun. 14, 2022. https://www.businesswire.com/news/home/20220613005701/en/Beckley-Psytech-Announces-Partnership-With-Ksana-Health-Building-on-Digital-Strategy-to-Deliver-Optimised-Patient-Outcomes. (3 pages).
"Beckley Psytech announces positive initial data from Phase IIa study of novel 5-MeO-DMT formulation BPL-003 for Treatment Resistant Depression," Mar. 27, 2024. https://www.businesswire.com/news/home/20240326357401/en/Beckley-Psytech-announces-positive-initial-data-from-Phase-IIa-study-of-novel-5-MeO-DMT-formulation-BPL-003-for-Treatment-Resistant-Depression. (3 pages).
"Beckley Psytech announces strategic investment from atai Life Sciences to accelerate the clinical development of short-duration psychedelics," Beckley Psytech Press Release Jan. 4, 2024 (10 pages).
"Beckley Psytech announces £14m raise to conduct clinical trials on psychedelic medicine pipeline," Beckley Psytech Press Release Dec. 22, 2020 (5 pages).
"Beckley Psytech applies for B Corporation status as part of its commitment to have a positive impact on society," Beckley Psytech Press Release Dec. 21, 2021 (5 pages).
"Beckley Psytech appoints Dr Rob Hershberg to its Board of Directors," Beckley Psytech Press Release Jun. 24, 2024 (6 pages).
"Beckley Psytech completes oversubscribed $80m (£58m) fundraise to develop portfolio of psychedelic medicine breakthroughs," Beckley Psytech Press Release Aug. 16, 2021 (3 pages).
"Beckley Psytech grows team with new Clinical Operations and Communications hires," Beckley Psytech Press Release Oct. 18, 2022 (4 pages).
"Beckley Psytech initiates Phase IIa study of 5-MeO-DMT candidate BPL-003 for Alcohol Use Disorder," Apr. 5, 2023. https://www.businesswire.com/news/home/20230405005132/en/Beckley-Psytech-initiates-Phase-IIa-study-of-5-MeO-DMT-candidate-BPL-003-for-Alcohol-Use-Disorder. (2 pages).
"Beckley Psytech Launches Phase IIa Study of Lead Candidate BPL-003, a Novel Benzoate Formulation of 5-MeO-DMT, for Treatment Resistant Depression," Dec. 21, 2022. https://www.businesswire.com/news/home/20221221005221/en/Beckley-Psytech-Launches-Phase-IIa-Study-of-Lead-Candidate-BPL-003-a-Novel-Benzoate-Formulation-of-5-MeO-DMT-for-Treatment-Resistant-Depression. (2 pages).
"Beckley Psytech publishes peer-reviewed paper on 5-MeO-DMT in Journal of Psychopharmacology," Beckley Psytech Press Release Feb. 22, 2022 (4 pages).
"Beckley Psytech receives approval for clinical trial using psychedelic agent to treat severe headache condition," Beckley Psytech Press Release Jan. 27, 2021 (4 pages).
"Beckley Psytech receives FDA Investigational New Drug (IND) approval for Phase IIb study of BPL-003, a novel synthetic formulation of 5-MeO-DMT (Mebufotenin)," Feb. 21, 2023. https://www.businesswire.com/news/home/20230221005523/en/Beckley-Psytech-receives-FDA-Investigational-New-Drug-IND-approval-for-Phase-IIb-study-of-BPL-003-a-novel-synthetic-formulation-of-5-MeO-DMT-Mebufotenin. (2 pages).
"Beckley Psytech Strengthens Pipeline and Development Team With Acquisition of Eleusis Therapeutics Limited," Oct. 24, 2022. https://www.businesswire.com/news/home/20221023005029/en/Beckley-Psytech-Strengthens-Pipeline-and-Development-Team-With-Acquisition-of-Eleusis-Therapeutics-Limited. (3 pages).
"Beckley Psytech Strengthens Senior Leadership Team With Appointment of Dr. Laura Trespidi as Chief Development Officer," May 24, 2022. https://www.businesswire.com/news/home/20220523005870/en/Beckley-Psytech-Strengthens-Senior-Leadership-Team-With-Appointment-of-Dr.-Laura-Trespidi-as-Chief-Development-Officer. (4 pages).
"Beckley Psytech Successfully Completes Phase I Clinical Study of Lead Candidate BPL-003, a Novel Benzoate Formulation Of 5-MeO-DMT," Nov. 15, 2022. https://www.businesswire.com/news/home/20221114005907/en/Beckley-Psytech-Successfully-Completes-Phase-I-Clinical-Study-of-Lead-Candidate-BPL-003-a-Novel-Benzoate-Formulation-Of-5-MeO-DMT. (2 pages).
"Beckley Psytech to attend 11th Annual LifeSci Partners Virtual Corporate Access Event," Dec. 8, 2021. https://www.businesswire.com/news/home/20211207006217/en/Beckley-Psytech-to-attend-11th-Annual-LifeSci-Partners-Virtual-Corporate-Access-Event. (2 pages).
"Beckley Psytech to Attend and Present at 8th Annual LSX World Congress 2022," Apr. 13, 2022. https://www.businesswire.com/news/home/20220412005773/en/Beckley-Psytech-to-Attend-and-Present-at-8th-Annual-LSX-World-Congress-2022. (2 pages).
"Beckley Psytech to Attend and Present at the Jefferies London Healthcare Conference - November 15-17. 2022," Nov. 4, 2022. https://www.businesswire.com/news/home/20221104005095/en/Beckley-Psytech-to-Attend-and-Present-at-the-Jefferies-London-Healthcare-Conference-%E2%80%93-November-15-17-2022. (2 pages).
"Beckley Psytech to participate in Canaccord Genuity's Symposium on New Paradigms and Treatment Approaches in Mental Health—Dec. 13, 2022," Beckley Psytech Press Release Dec. 7, 2022 (4 pages).
"Beckley Psytech to Present at 32nd Annual Oppenheimer Healthcare Conference," Mar. 10, 2022. https://www.businesswire.com/news/home/20220309005837/en/Beckley-Psytech-to-Present-at-32nd-Annual-Oppenheimer-Healthcare-Conference. (2 pages).
"Beckley Psytech to present at H.C. Wainwright 2nd Annual Psychedelics Conference and Stifel 2nd Annual Conference "The Future of Healthcare"," Dec. 2, 2021. https://www.businesswire.com/news/home/20211201006018/en/Beckley-Psytech-to-present-at-H.C.-Wainwright-2nd-Annual-Psychedelics-Conference-and-Stifel-2nd-Annual-Conference-%E2%80%9CThe-Future-of-Healthcare%E2%80%9D. (2 pages).
"Beckley Psytech to present at Jefferies 2021 London Healthcare Conference," Nov. 2, 2021. https://www.businesswire.com/news/home/20211102005131/en/Beckley-Psytech-to-present-at-Jefferies-2021-London-Healthcare-Conference. (2 pages).
"Beckley Psytech to present data from Phase I study of BPL-003, a novel synthetic formulation of 5-MeO-DMT (Mebufotenin), at upcoming scientific conference," Beckley Psytech Press Release Apr. 24, 2023 (5 pages).
"Beckley Psytech's Phase I study results of novel 5-MeO-DMT formulation BPL-003 published in The Journal of Psychopharmacology," Beckley Psytech Press Release Apr. 17, 2024 (6 pages).
"Brunch with Sifted: Amanda Feilding and Cosmo Feilding-Mellen on the psychedelic renaissance," Beckley Psytech Press Release Nov. 24, 2021 (13 pages).
"Cimarec+ stirrers, hotplates, and stirring hotplates: Operating Manual and Parts List," Thermo Scientific (Feb. 2017) (31 pages).
"Clinical Practice Guideline: Intranasal Medication Administration," Emergency Nurses Association. (36 pages) (2016).

(56) References Cited

OTHER PUBLICATIONS

"Clomipramine," <https://www.drugs.com/monograph/clomipramine.html>, medically reviewed on May 22, 2024 (16 pages).
"Cosmo Feilding Mellen on Beckley Psytech's plans for 2021," Beckley Psytech Press Release Apr. 12, 2021 (6 pages).
"Dr Frank Wiegand, Experienced Neuroscience Leader Joins Beckley Psytech as Chief Medical Officer," Nov. 3, 2021. https://www.businesswire.com/news/home/20211103005056/en/Dr-Frank-Wiegand-Experienced-Neuroscience-Leader-Joins-Beckley-Psytech-as-Chief-Medical-Officer. (2 pages).
"Enhancing the accessibility of psychedelic healthcare," Beckley Psytech Press Release Nov. 23, 2021 (7 pages).
"European companies set to dominate psychedelics market," Beckley Psytech Press Release Mar. 1, 2021 (12 pages).
"First participant dosed in research study investigating the effects of BPL-003, a novel formulation of 5-MeO-DMT, on the human brain," Beckley Psytech Press Release Jun. 3, 2024 (6 pages).
"First patient dosed in Beckley Psytech's international Phase IIb study of BPL-003, a novel synthetic intranasal formulation of 5-MeO-DMT, for Treatment Resistant Depression (TRD)," Beckley Psytech Press Release Oct. 24, 2023 (6 pages).
"First Patient Dosed in Beckley Psytech's Phase IIa Study of BPL-003 for Treatment Resistant Depression," May 4, 2023. https://www.businesswire.com/news/home/20230504005020/en/First-Patient-Dosed-in-Beckley-Psytech%E2%80%99s-Phase-lla-Study-of-BPL-003-for-Treatment-Resistant-Depression. (2 pages).
"First patient dosed in Beckley Psytech's Phase IIa study of BPL-003 in combination with SSRIs for Treatment Resistant Depression," Beckley Psytech Press Release Apr. 24, 2024 (6 pages).
"Former GW Pharmaceuticals CFO joins Beckley Psytech's Board," Beckley Psytech Press Release Apr. 13, 2021 (4 pages).
"Global Investors Back Psychedelic Medicine Start-Up With $3.8m Series A Round," Beckley Psytech Press Release Jun. 30, 2020 (9 pages).
"Investors think mind-bending drug DMT could rival psilocybin as a cost-effective psychedelic treatment for conditions like depression. 3 VCs explain why its fast-acting properties are appealing," Beckley Psytech Press Release May 30, 2021 (3 pages).
"Learning from 50 years of psychedelic progress," Psytech Press Release Oct. 19, 2020 (6 pages).
"Meet our new scientific advisors," Psytech Press Release Nov. 6, 2020 (4 pages).
"Meet our new Scientific Advisory Board!," Beckley Psytech Press Release Sep. 10, 2020 (6 pages).
"N-[2-(1-methyl-1H-indol-3-yl)ethyl]oxan-4-amine," Chemazone. Product No. 171.355.434, retrieved Oct. 24, 2024 (2021) (4 pages).
"N-[2-(1H-indol-3-yl)ethyl]oxan-4-amine," National Library of Medicine. PubChem CID: 43608479, retrieved Oct. 25, 2024 (2009) (7 pages).
"New psychedelic medicine COO looks to boost pharma and biotech collaborations," Beckley Psytech Press Release 2.22.21 (4 pages).
"Prescribe Software for Mental Health Treatment," Beckley Psytech Press Release Jun. 16, 2021 (6 pages).
"Psychedelic Compounds Chemical and Physical Properties," <https://wiki.dmt-nexus.me/Psychedelic_Compounds_Chemical_and_Physical_Properties>, last modified on May 19, 2023 (18 pages).
"Psychedelics breakthroughs—why now?," Beckley Psytech Press Release Sep. 10, 2020 (6 pages).
"Quiet! Seed Crystals Growing," Flinn Scientific Inc, <https://www.flinnsci.com/api/library/Download/fcd83e5a579b470f9c0acc678ac6564c>, (6 pages) (2017).
"Researchers In Europe, U.S. Team Up To Produce First Ever 5-MeO-DMT Psychedelic Training Program," Beckley Psytech Press Release Apr. 19, 2021 (8 pages).
"Seed crystal," <https://web.archive.org/web/20201209202659/https://en.wikipedia.org/wiki/Seed_crystal>, last modified Mar. 29, 2020 (2 pages).
"Spotlight on Beckley Psytech and psilocybin," Beckley Psytech Press Release Mar. 22, 2021 (5 pages).
"Spotlight on the psychedelic experience," Beckley Psytech Press Release Jun. 9, 2021 (5 pages).
"SPRAVATO (esketamine) nasal spray, CIII." Janssen Pharmaceuticals, prescribing information. Jul. 2020 (15 pages).
"Thermal Applications Note: Purge Gas Recommendations for use in Modulated DSC," Ta Instruments: Thermal Analysis & Rheology (3 pages).
"This psychedelic medicine company wants to treat psychiatric and neurological disorders," Psytech Press Release Dec. 21, 2020 (5 pages).
"Understanding 5-MeO-DMT: Historical use," Beckley Psytech Press Release Mar. 11, 2021 (5 pages).
"Vacuum for Laboratories: Vacuu-Lan Local Vacuum Networks," Vacuubrand (2019) (16 pages).
"Wearable technology can revolutionise our clinical research," Beckley Psytech Press Release Mar. 2, 2021 (5 pages).
"Woman who has suffered with a non-stop headache for eight years fulfils dream of becoming a mum," Beckley Psytech Press Release Mar. 2, 2021 (8 pages).
Akai et al., "Anxiolytic effects of lisuride and its agonistic action to central 5-HT1A receptors," Nihon Yakurigaku Zasshi. 97(4):209-20 (English Abstract Included) (Apr. 1991).
Carhart-Harris et al., "Psilocybin with psychological support for treatment-resistant depression: an open-label feasibility study," Lancet Psychiatry 3(7):619-27 (2016).
Family et al., "Safety, tolerability, pharmacokinetics, and pharmacodynamics of low dose lysergic acid diethylamide (LSD) in healthy older volunteers," Psychopharmacology. 237(3):841-853 (13 pages) (Dec. 2019).
Fanciullacci et al., "Brief report: Phantom limp pain: sub-hallucinogenic treatment with lysergic acid diethylamide (LSD-25)," Headache 17(3):118-9 (Jul. 1977).
Greenan et al., "Preparation and Characterization of Novel Crystalline Solvates and Polymorphs of Psilocybin and Identification of Solid Forms Suitable for Clinical Development," ResearchGate (Feb. 2020) (29 pages).
Griffiths et al., "Psilocybin produces substantial and sustained decreases in depression and anxiety in patients with life-threatening cancer: A randomized double-blind trial," J Psychopharmacol. 30(12): 1181-97 (Dec. 2016).
Haridy, Rich, "The start-up behind a magic mushroom nose spray for psychedelic microdosing," New Atlas. Dec. 5, 2019 (12 pages).
Kargbo et al., "Direct Phosphorylation of Psilocin Enables Optimized cGMP Kilogram-Scale Manufacture of Psilocybin," ACS Omega. 5(27): 16959-16966 (Jul. 2020).
Kargbo et al., "Psilocybin: Characterization of the Metastable Zone Width (MSZW), Control of Anhydrous Polymorphs, and Particle Size Distribution (Psd)," Acs Omega. 7(6): 5429-5436 (Feb. 2022) with supporting information.
Kooijman et al., "Are psychedelics the answer to chronic pain: A review of currentliterature," Pain Pract. 23(4): 447-458 (Apr. 2023).
Malik et al., "Phase 1 Study Results on the Effects of 5-MeO-DMT Benzoate on Facial Emotion Processing in Psychedelic-Naïve Healthy Subjects," Neuroscience Applied 2. P.0097:45-46 (2 pages).
Malik et al., "Phase 1 study results on the effects of 5-MeO-DMT. benzoate (BPL-003) on facial emotion processing in psychedelic-naïve healthy subjects," Beckley Psytech. Poster No. p. 0097. Presented: Sep. 30, 2023 (1 page).
Marek et al., "The selective 5-HT2A receptor antagonist M100907 enhances antidepressant-like behavioral effects of the SSRI fluoxetine," Neuropsychopharmacology. 30(12):2205-2015 (Dec. 2005).
Monson et al., "MDMA-facilitated cognitive-behavioural conjoint therapy for posttraumatic stress disorder: an uncontrolled trial," Eur J Psychotraumatol. 11(1): 1840123 (Dec. 7, 2020).
Monte et al., "Stereoselective LSD-like activity in a series of d-lysergic acid amides of (R)- and (S)- 2-aminoalkanes," J Med Chem. 38(6):958-66 (Mar. 17, 1995).
Passie et al., "The pharmacology of lysergic acid diethylamide: a review," CNS Neurosci Ther. 14(4):295-314 (2008) (20 pages).
PharmaTher Holdings Ltd. Dec. 14, 2021. PharmaTher Announces Positive Research Results for LSD Microneedle Patch. Press Release. <URL: https://psychedelicinvest.com/pharmather-announces-positive-research-results-for-lsd-microneedle-patch/> (6 pages).

(56) References Cited

OTHER PUBLICATIONS

Reckweg et al., "A Phase 1, Dose-Ranging Study to Assess Safety and Psychoactive Effects of a Vaporized 5-Methoxy-N,N-Dimethyltryptamine Formulation (GH001) in Healthy Volunteers," Front Pharmacol. 12 (760671) (12 pages) (Nov. 2021).

Reckweg et al., "A phase 1/2 trial to assess safety and efficacy of a vaporized 5-methoxy-N,N-dimethyltryptamine formulation (GH001) in patients with treatment-resistant depression," Front Psychiatry. (8 pages) (Jun. 2023).

Roberts et al., "Intranasal 5-MeO-DMT (BPL-003) safety, pharmacokinetics and psychedelic effects in healthy volunteers," Beckley Psytech. Poster No. P.0639. Presented: 6th ECNP Congress, Barcelona, Spain, Oct. 7-10, 2023 (1 page).

Roberts et al., "Intranasal 5-Methoxy-N, N-Dimethyltryptamine Safety, Pharmacokinetics and Psychedelic Effects in Healthy Volunteers," Neuroscience Applied 2. P.0639:6-7 (2 pages).

Robertson, Dr. Donald L., "Supersaturated Solution," modified Oct. 18, 2010 (1 page).

Roseman et al., "Increased amygdala responses to emotional faces after psilocybin for treatment-resistant depression," Neuropharmacology 142:263-9 (Nov. 2018).

Rucker et al., "Intranasal 5-MeO-DMT (BPL-003) Safety, PK, and effect on altered states of consciousness in healthy volunteers," Beckley Psytech. Poster No. T152. Presented: SOBP Annual Meeting, San Diego, California, Apr. 27-29, 2023 (1 page).

Rucker et al., "Phase 1, placebo-controlled, single ascending dose trial to evaluate the safety, pharmacokinetics and effect on altered states of consciousness of intranasal BPL-003 (5-methoxy- N,N-dimethyltryptamine benzoate) in healthy participants," J. Psychopharmacol. Clinical Trial 38(8): 712-723 (Aug. 2024).

Sherwood et al., "Psilocybin: crystal structure solutions enable phase analysis of prior art and recently patented examples," Acta Crystallogr C Struct Chem. 78(Pt 1):36-55 (Jan. 2022).

Szabo et al., "Psychedelic N, N-dimethyltryptamine and 5-methoxy-N,N-dimethyltryptamine modulate innate and adaptive inflammatory responses through the sigma-1 receptor of human monocyte-derived dendritic cells," PLoS One 9(8):e106533 (12 pages) (Aug. 29, 2014).

Turton et al., "A qualitative report on the subjective experience of intravenous psilocybin administered in an FMRI environment," Curr Drug Abuse Rev. 7(2):117-127 (2014).

Tyles et al., "Psilocybin—summary of knowledge and new perspectives," Eur Neuropsychopharmacol. 24(3): 342-56 (Mar. 2014).

Uthaug et al., "Prospective examination of synthetic 5-methoxy-N, N-dimethyltryptamine inhalation: effects on salivary IL-6, cortisol levels, affect, and non-judgment," Psychopharmacology (Berl). 237(3):773-85 (Mar. 2020).

Whelan et al., "Lysergic acid diethylamide and psilocybin for the management of patients with persistent pain: a potential role?," Pain Manag. 8(3):217-29 (May 2018).

Wolfson et al., "MDMA-assisted psychotherapy for treatment of anxiety and other psychological distress related to life-threatening illnesses: a randomized pilot study," Sci Rep. 10(1):20442 (15 pages) (Nov. 24, 2020).

Yazar-Klosinski et al., "Potential Psychiatric Uses for MDMA," Clin Pharmacol Ther. 101(2):194-6 (Feb. 2017).

Lieberman et al., "Lisuride in Parkinson disease: efficacy of lisuride compared to levodopa," Neurology. 31(8):961-5. Abstract (Aug. 1981).

Nakamura et al., "Effects in animal models of depression of lisuride alone and upon coadministration with antidepressants," Folia pharmacol japon. 94(1):81-9 (English language abstract) (1989).

Katzman, Martin A., "Aripiprazole: A clinical review of its use for the treatment of anxiety disorders and anxiety as a comorbidity in mental illness," Journal of Affective Disorders. 128S1:S11-20 (2011).

ERGOLINE ANALOGUES

CROSS-REFERENCE TO RELATED APPLICATIONS

This application is a continuation of U.S. application Ser. No. 17/932,854, filed on Sep. 16, 2022, which is a continuation of U.S. application Ser. No. 17/941,506, filed on Sep. 9, 2022, now U.S. Pat. No. 11,697,651, which is a continuation of International Application No. PCT/IB2022/050355, filed on Jan. 17, 2022, each of which is incorporated by reference herein, PCT/IB2022/050355 claiming the benefit of priority to GB Application No. 2100549.1, filed on Jan. 15, 2021, GB Application No. 2107104.8, filed on May 18, 2021, and GB Application No. 2116270.6, filed on Nov. 11, 2021.

FIELD OF THE INVENTION

This invention relates to pharmaceutically acceptable ergoline analogues and salts thereof. In particular, though not exclusively, the invention relates to formulations and uses of the same as a medicament.

BACKGROUND TO THE INVENTION

Ergoline is the main structure for a class of alkaloids including the well-known lysergic acid diethylamide (LSD). The chemical formula of LSD is:

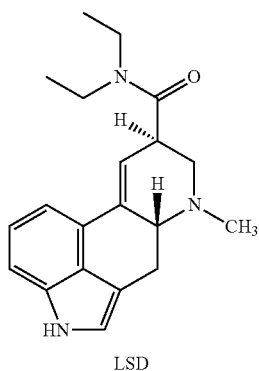

LSD

Various synthetic modifications to the structure of LSD have been made in the prior art. However, such modifications often result in a decrease in activity. Ineffective docking/binding of these compounds to the appropriate receptors may result from such structural modifications.

There remains a need in the art for ergoline analogues, and improved compositions and uses thereof.

SUMMARY

Herein disclosed is a compound of Formula (I) wherein:

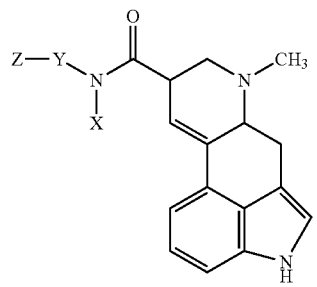

(I)

X is selected from H or $C_{1-6}$ alkyl (optionally, X is methyl or isopropyl); and
Y is selected from a bond, O, CONH, NH, N($C_{1-6}$ alkyl), A-$(CH_2)_n$—B, wherein
A is O, NH or N($C_{1-6}$ alkyl), wherein
B is a bond, O, or NH, wherein
n is 1 to 4; and
Z is selected from H, OH, $NH_2$, $NHC_{1-6}$ alkyl, N($C_{1-6}$ alkyl)$_2$, $C_{1-6}$ alkyl, $C_{6-10}$ aryl, $SO_2$—$C_{1-6}$ alkyl, $SO_2$—$C_{5-10}$ aryl, $C_3$-$C_{10}$ heteroaromatic or heterocyclic group comprising one, two or three heteroatoms independently selected from O and N; and
wherein X and Z are different;
or is a pharmaceutically acceptable salt thereof.

In a first aspect of the invention, there is provided compound of Formula (I) wherein:

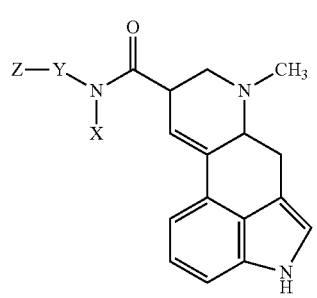

(I)

X is selected from methyl or isopropyl; and
Y is selected from a bond, O, CONH, NH, N($C_{1-6}$ alkyl), A-$(CH_2)_n$—B, wherein
A is O, NH or N($C_{1-6}$ alkyl), wherein
B is a bond, O, or NH, wherein
n is 1 to 4; and
Z is selected from H, OH, $NH_2$, $NHC_{1-6}$ alkyl, N($C_{1-6}$ alkyl)$_2$, $C_{1-6}$ alkyl, $C_{6-10}$ aryl, $SO_2$—$C_{1-6}$ alkyl, $SO_2$—$C_{5-10}$ aryl, $C_3$-$C_{10}$ heteroaromatic or heterocyclic group comprising one, two or three heteroatoms independently selected from O and N; and
wherein X and Z are different;
or a pharmaceutically acceptable salt thereof.

In an embodiment the alkyl group is straight, branched or a cyclic alkyl group.

In an embodiment the alkyl group is a straight chain alkyl group. In an embodiment the alkyl group contains 1, 2 or 3 halogens.

In an embodiment X is methyl.
In an embodiment X is isopropyl.
In an embodiment Y is selected from a bond, O, CONH, NH or NCH$_3$.
In an embodiment Y is A-(CH$_2$)$_n$—B, wherein
A is O or NH, wherein
B is a bond, O or NH, wherein
n is 1 to 4.
In an embodiment n is 2 or 3.
In an embodiment Z is selected from pyridine, morpholine, SO$_2$—CH$_3$, SO$_2$-phenyl, 8-oxa-3-azabicyclo[3.2.1]octane and 2-oxa-5-azabicyclo[2.2.1]heptane.
In an embodiment Y—Z together form the group:

O—(CH$_2$)$_3$—N(CH$_3$)$_2$

NH—(CH$_2$)$_2$—OH

NH—(CH$_2$)$_3$—OH

NH—(CH$_2$)$_3$—OCH$_3$

NH—(CH$_2$)$_3$—SO$_2$CH$_3$

NH—(CH$_2$)$_2$—NH—SO$_2$CH$_3$, or

O—(CH$_2$)$_2$—NH—SO$_2$CH$_3$.

In an embodiment Y—Z together form the group:
NH-phenyl, pyridine, O-morpholine, NH-morpholine, NH—SO$_2$-Phenyl, NCH$_3$—SO$_2$-Phenyl, CONH-Phenyl, 8-oxa-3-azabicyclo[3.2.1]octane or 2-oxa-5-azabicyclo[2.2.1]heptane.

In an embodiment there is provided one or more compounds selected from:

| Number | IUPAC | SMILES | Structure |
|---|---|---|---|
| 001 | (1S,2R)-2-(1H-indol-3-yl)cyclopropan-1-aminium | [H]N1C([H])=C(C2=C1C([H])=C([H])C([H])=C2[H])[C@@]1([H])C([H])([H])[C@]1([H])[N+]([H])([H])[H] | 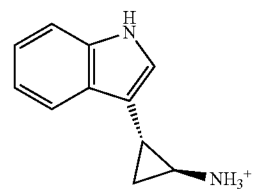 [SMILES: [NH3+][C@H]1C[C@@H]1c1c[nH]c2ccccc12] |
| 002 | (4R,6R,7R)-4-[N'-(3-hydroxypropyl)-N-methylhydrazinecarbonyl]-6-methyl-6,11-diazatetracyclo[7.6.1.0$^{2,7}$.0$^{12,16}$]hexadeca-1(16),2,9,12,14-pentaen-6-ium | [H]OC([H])([H])C([H])([H])C([H])([H])N([H])N(C(=O)[C@]1([H])C([H])=C2C3=C4C(N([H])C([H])=C4C([H])([H])[C@@]2([H])[N@+]([H])(C([H])[H])[H])C1([H])[H])=C([H])C([H])=C3[H])C([H])([H])[H] | 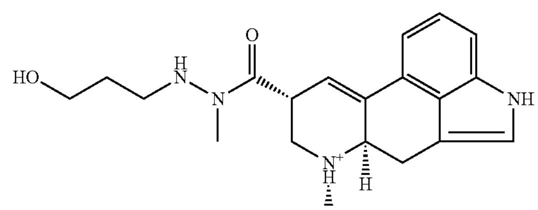 |
| 003 | (4R,6R,7R)-6-methyl-4-[methyl(pyridin-4-yl)carbamoyl]-6,11-diazatetracyclo[7.6.1.0$^{2,7}$.0$^{12,16}$]hexadeca-1(16),2,9,12,14-pentaen-6-ium | [H]N1C([H])=C2C3=C(C([H])=C([H])C([H])=C13)C1=C([H])[C@@]([H])(C(=O)N(C3=C([H])C([H])=NC([H])=C3[H])C([H])([H])[H])C([H])([H])[N@@+]([H])(C([H])([H])[H])[C@]1([H])C2([H])[H] | 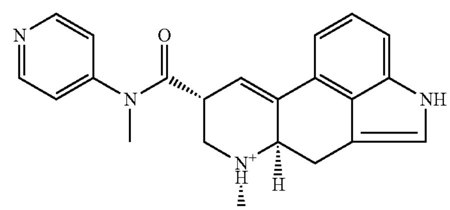 |
| 004 | (4R,6R,7R)-6-methyl-4-[N-methyl-N'-(oxan-4-yl)hydrazinecarbonyl]-6,11-diazatetracyclo[7.6.1.0$^{2,7}$.0$^{12,16}$]hexadeca-1(16),2,9,12,14-pentaen-6-ium | [H]N(N(C(=O)[C@]1([H])C([H])=C2C3=C4C(N([H])C([H])=C4C([H])([H])[C@@]2([H])[N@+])([H])(C([H])([H])[H])C1([H])[H])=C([H])C([H])=C3[H])C([H])([H])[H])C1([H])C([H])([H])C([H])([H])OC([H])([H])C1([H])[H] | 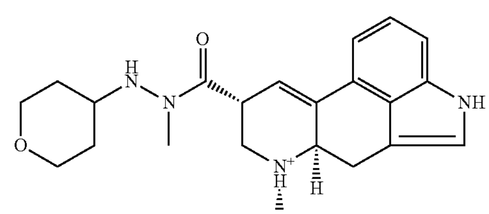 |
| 005 | (4R,6R,7R)-4-[N'-(benzenesulfonyl)-N,N'-dimethylhydrazinecarbonyl]-6-methyl-6,11-diazatetracyclo[7.6.1.0$^{2,7}$.0$^{12,16}$]hexadeca-1(16),2,9,12,14-pentaen-6-ium | [H]N1C([H])=C2C3=C(C([H])=C([H])C([H])=C13)C1=C([H])[C@@]([H])(C(=O)N(N(C([H])([H])[H])S(=O)(=O)C3=C([H])C([H])=C([H])C([H])=C3[H])C([H])([H])[H])[H])C([H])([H])[N@@+]([H])(C([H])([H])[H])[C@]1([H])C2([H])[H] | 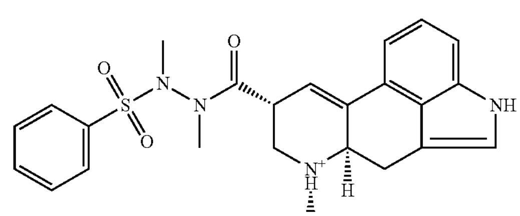 |

-continued

| Number | IUPAC | SMILES | Structure |
|---|---|---|---|
| 006 | (4R,6R,7R)-4-[N'-(3-methoxypropyl)-N-methylhydrazine-carbonyl]-6-methyl-6,11-diazatetra-cyclo[7.6.1.0²,⁷.0¹²,¹⁶]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+])[H])(C([H])([H])[H])C1)[H])[H])=C([H])C([H])=C3[H])C([H])([H])[H])C)[H])([H])C([H])([H])C([H])([H])OC([H])([H])[H] | 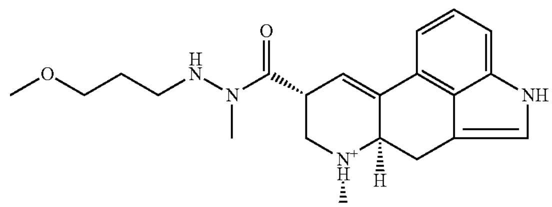 |
| 007 | (4R,6R,7R)-6-methyl-4-{methyl[(1R,5S)-8-oxa-3-aza-bicyclo[3.2.1]octan-3-yl]carbamoyl}-6,11-diazatetra-cyclo[7.6.1.0²,⁷.0¹²,¹⁶]hexadeca-1(16),2,9,12,14-pentaen-6-ium | [H]N1C([H])=C2C3=C(C([H])=C([H])C([H])=C13)C1=C([H])[C@@]([H])(C(=O)N(N3C([H])([H])[C@@]4([H])O[C@]([H])(C([H])([H])C4([H])[H])C3([H])[H])C([H])([H]))[H]C([H])([H])[N@@+]([H])(C([H])([H])[H])[C@]1([H])C2([H])[H] | 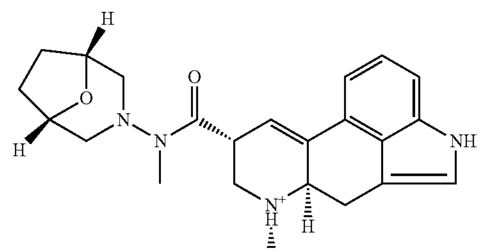 |
| 008 | (4R,6R,7R)-6-methyl-4-[methyl(oxan-4-yloxy)carbamoyl]-6,11-diazatetra-cyclo[7.6.1.0²,⁷.0¹²,¹⁶]hexadeca-1(16),2,9,12,14-pentaen-6-ium | [H]N1C([H])=C2C3=C(C([H])=C([H])C([H])=C13)C1=C([H])[C@@]([H])(C(=O)N(OC3([H])C([H])([H])C([H])([H])OC([H])([H])C3([H])[H])C([H]))[H])[H])C([H])([H])[N@@+]([H])(C([H])([H])[H])[C@]1([H])C2([H])[H] | 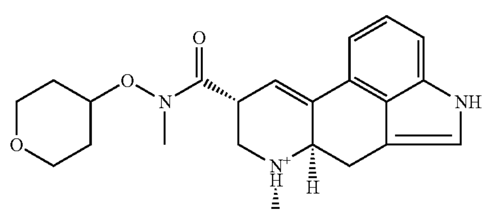 |
| 009 | (4R,6R,7R)-4-[N'-(benzenesulfonyl)-N-methylhydrazine-carbonyl]-6-methyl-6,11-diazatetra-cyclo[7.6.1.0²,⁷.0¹²,¹⁶]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+])[H])(C([H])([H])[H])C1)[HJ][H])=C([H])C([H])=C3[H])C([H])([H])[H])S(=O)(=O)C1=C([H])C([H])=C([H])C([H])=C1[H] | 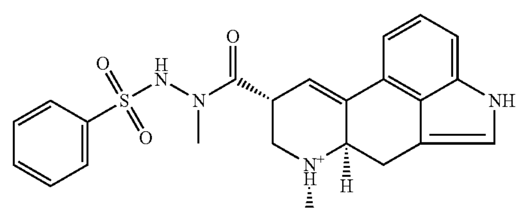 |
| 010 | (4R,6R,7R)-4-[N'-(3-methanesulfonylpropyl)-N-methylhydrazine-carbonyl]-6-methyl-6,11-diazatetra-cyclo[7.6.1.0²,⁷.0¹²,¹⁶]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+])[H])(C([H])([H])[H])C1)[H])[H])=C([H])C([H])=C3[H])C([H])([H])[H])C)[H])([H])C([H])([H])C([H])([H])S(=O)(=O)C([H])([H])[H] | 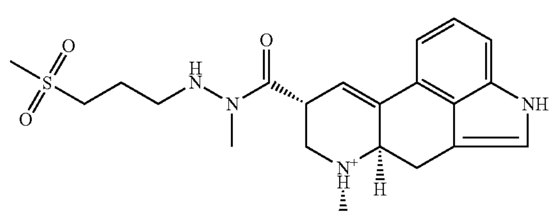 |
| 011 | (4R,6R,7R)-6-methyl-4-{[methyl(phenyl-carbamoyl)amino]carbonyl}-6,11-diazatetra-cyclo[7.6.1.0²,⁷.0¹²,¹⁶]hexadeca-1(16),2,9,12,14-pentaen-6-ium | [H]N(C(=O)N(C(=O)[C@]1([H])C([H])=C2C3=C4C(N([H])C([H])=C4C([H])([H])[C@@]2([H])[N@+])(HJ)C([H])([H])[H])C1([H])[H])=C([H])C([H])=C3[H])C([H])([H])[H])C1=C([H])C([H])=C([H])C([H])=C1[H] | 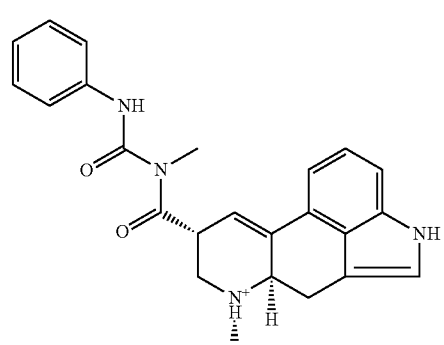 |

-continued

| Number | IUPAC | SMILES | Structure |
|---|---|---|---|
| 012 | (4R,6R,7R)-4-[N'-(2-methanesulfonamidoethyl)-N-(propan-2-yl)hydrazinecarbonyl]-6-methyl-6,11-diazatetracyclo[7.6.1.0²,⁷.0¹²,¹⁶]hexadeca-1(16),2,9,12,14-pentaen-6-ium | [H]N(N(C(=O)[C@]1([H])C([H])=C2C3=C4C(N)([H])C([H])=C4C([H])([H])[C@@]2([H])[N@+])[H])(C([H])([H])[H])C1)([H])[H])=C([H])C([H])=C3[H])C([H])(C([H])([H])[H])C([H])([H])[H])C([H])([H])C([H])([H])[H])N([H])S(=O)(=O)C([H])([H])[H] | 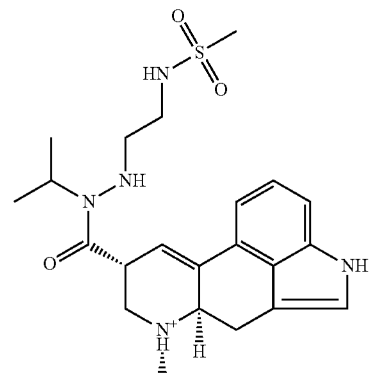 |
| 013 | (4R,6R,7R)-4-[N'-(2-hydroxyethyl)-N-(propan-2-yl)hydrazinecarbonyl]-6-methyl-6,11-diazatetracyclo[7.6.1.0²,⁷.0¹²,¹⁶]hexadeca-1(16),2,9,12,14-pentaen-6-ium | [H]OC([H])([H])C([H])([H])N([H])N(C(=O)[C@]1([H])C([H])=C2C3=C4C(N([H])C([H])=C4C([H])([H])[C@@]2([H])[N@+]([H])C([H])([H])[H])C1([H])[H])=C([H])C([H])=C3[H])C([H])(C([H]))[H])[H])C([H])([H])[H] | 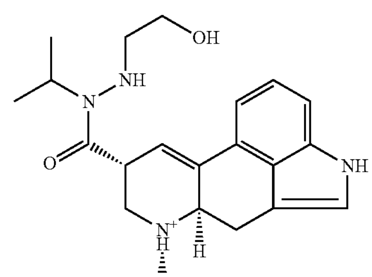 |
| 014 | (4R,6R,7R)-6-methyl-4-{[(1S,4S)-2-oxa-5-azabicyclo[2.2.1]heptan-5-yl](propan-2-yl)carbamoyl}-6,11-diazatetracyclo[7.6.1.0²,⁷.0¹²,¹⁶]hexadeca-1(16),2,9,12,14-pentaen-6-ium | [H]N1C([H])=C2C3=C(C([H])=C([H])C([H])=C13)C1=C([H])[C@@]([H])(C(=O)N(N3C([H])([H])[C@@]4([H])OC([H])[H])[C@]3([H])C4([H])[H])C([H])(C([H])([H])[H])C([H])([H])[H])C([H])([H])[N@@+]([H])(C([H]))[H])[H])[C@]1([H])C2)[H])[H] | 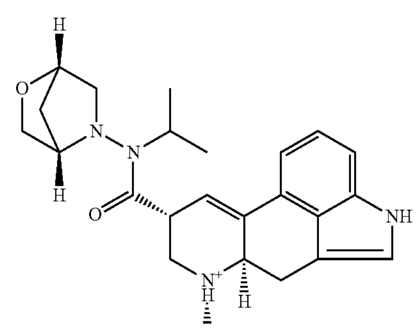 |
| 015 | (4R,6R,7R)-6-methyl-4-{[(1S,4S)-2-oxa-5-azabicyclo[2.2.2]octan-5-yl](propan-2-yl)carbamoyl}-6,11-diazatetracyclo[7.6.1.0²,⁷.0¹²,¹⁶]hexadeca-1(16),2,9,12,14-pentaen-6-ium | [H]N1C([H])=C2C3=C(C([H])=C([H])C([H])=C13)C1=C([H])[C@@]([H])(C(=O)N(N3C([H])([H])[C@@]4([H])OC([H])([H])[C@]3([H])C([H])([H])C4([H])[H])C([H])(C([H])([H])[H])C([H])([H])[H])C([H])([H])[N@@+]([H])(C([H])([H])[H])[C@]1([H])C2([H])[H] | 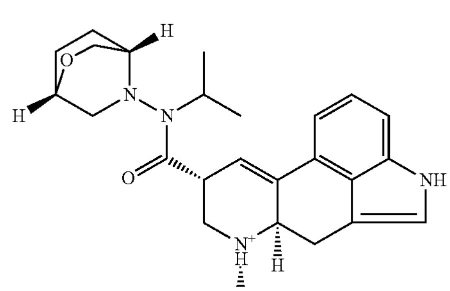 |

-continued

| Number | IUPAC | SMILES | Structure |
|---|---|---|---|
| 016 | (4R,6R,7R)-4-[(2-methanesulfonamido-ethoxy)(propan-2-yl)carbamoyl]-6-methyl-6,11-diazatetra-cyclo[7.6.1.0²,⁷.0¹²,¹⁶]hexadeca-1(16),2,9,12,14-pentaen-6-ium | [H]N(C([H])([H])C([H])([H])ON(C(=O)[C@]1([H])C([H])=C2C3=C4C(N)([H])C([H])=C4C([H])([H])[C@@]2([H])[N@+])([H])(C([H])([H])H)C1)([H])[H])=C([H])C([H])=C3[H])C([H])(C([H])([H])[H])C([H])([H])[H])S(=O)(=O)C([H])([H])[H] | 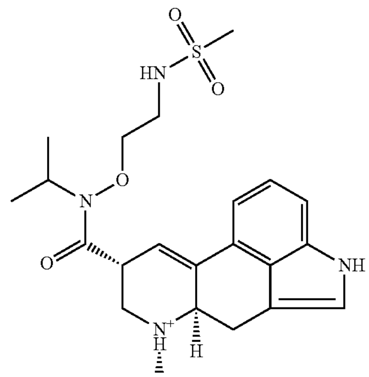 |
| 017 | (4R,6R,7R)-4-{[3-(dimethylazanium yl)propoxy](propan-2-yl)carbamoyl}-6-methyl-6,11-diazatetra-cyclo[7.6.1.0²,⁷.0¹²,¹⁶]hexadeca-1(16),2,9,12,14-pentaen-6-ium | [H]N1C([H])=C2C3=C(C([H])=C([H])C([H])=C13)C1=C([H])[C@@]([H])(C(=O)N(OC([H])([H])C([H])([H])C([H])([H])[N+]([H])(C([H])([H])[H])C)([H])[H])[H])C([H])(C([H])([H])[H])[H])C([H])([H])[H])C([H])([H])[N@@+][H])(C([H])([H])[H])[C@]1([H])C2([H])[H] | 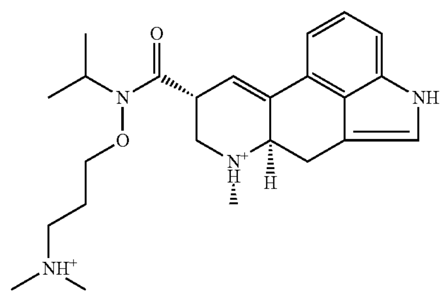 |
| 018 | (4R,6R,7R)-6-methyl-4-[pentyl(propan-2-yl)carbamoyl]-6,11-diazatetra-cyclo[7.6.1.0²,⁷.0¹²,¹⁶]hexadeca-1(16),2,9,12,14-pentaen-6-ium | [H]N1C([H])=C2C3=C(C([H])=C([H])C([H])=C13)C1=C([H])[C@@]([H])(C(=O)N(C([H])([H])C([H])([H])C([H])([H])C([H])([H])C([H])([H])[H])C([H])(C([H])([H])[H])C([H])([H])[H])[H])C([H])([H])[N@@+]([H])(C([H])([H])[H])[C@]1([H])C2([H])[H] | 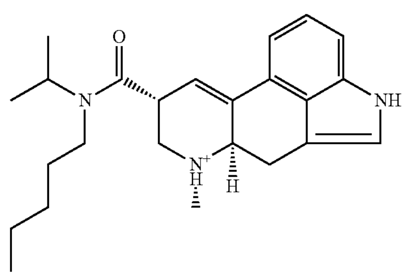 |
| 019 | (4R,6R,7R)-6-methyl-4-[(propan-2-yl)carbamoyl]-6,11-diazatetra-cyclo[7.6.1.0²,⁷⁷.0¹²,¹⁶]hexadeca-1(16),2,9,12,14-pentaen-6-ium | [H]N(C(=O)[C@]1([H])C([H])=C2C3=C4C(N[H])C([H])=C4C([H])([H])[C@@]2([H])[N@+]([H])(C([H])([H])[H])C1([H])[H])=C([H])C([H])=C3[H])C([H])(C([H])([H])[H])C([H])([H])[H] | 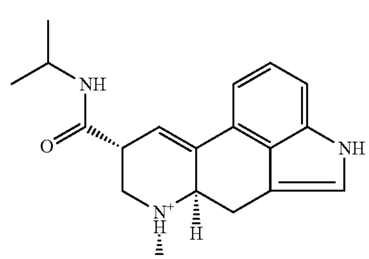 |

In an embodiment there is provided one or more compounds selected from:

| Number | Structure |
|---|---|
| 020 | (structure) |
| 021 | (structure) |
| 022 | (structure) |
| 023 | (structure) |
| 024 | (structure) |
| 025 | (structure) |

As calculated and described further herein below, compounds 001 to 019 have good 'Docking Scores' (Kcal/mol) to target the modelled receptors and are synthetically accessible. As such, compounds 001 to 019 are demonstrated to be synthetically accessible and useful as medicaments for appropriate conditions involving the target receptors, or related receptors with the associated corresponding conditions.

| Number | Synthetic Accessibility | Docking scores (Kcal/mol) |
|---|---|---|
| 001 | 2.35 | −8.579 |
| 002 | 4.39 | −13.446 |
| 003 | 4.19 | −12.761 |
| 004 | 4.55 | −12.399 |
| 005 | 4.72 | −12.957 |
| 006 | 4.51 | −12.330 |
| 007 | 5.63 | −12.323 |
| 008 | 4.62 | −12.549 |
| 009 | 4.59 | −12.506 |
| 010 | 4.64 | −11.908 |
| 011 | 4.43 | −12.275 |
| 012 | 4.84 | −12.818 |
| 013 | 4.51 | −12.370 |
| 014 | 5.76 | −12.593 |
| 015 | 5.89 | −12.395 |
| 016 | 4.92 | −12.366 |
| 017 | 4.98 | −12.362 |
| 018 | 4.62 | −12.146 |
| 019 | 4.09 | −11.855 |

In an embodiment there is provided a composition comprising a pharmaceutically effective amount of a compound as described previously.

In an embodiment, the nitrogen atom on the core six-membered ring is not methylated (e.g. Compound 025 is not methylated). In an embodiment, the nitrogen atom on the core six-membered ring is methylated (e.g. Compound 025 is methylated).

In an embodiment the composition comprises a dosage amount in the range of 0.05 mg to 100 mg.

In an embodiment the composition comprises a dosage amount in the range of 0.1 mg to 50 mg.

In an embodiment the composition comprises a dosage amount in the range of 0.5 mg to 25 mg.

In an embodiment the composition comprises a dosage amount in the range of 0.5 mg to 10 mg.

In an embodiment the composition comprises a dosage amount in the range of 1 mg to 10 mg.

In an embodiment the composition comprises a dosage amount in the range of 1 mg to 8 mg.

In an embodiment the composition comprises a dosage amount in the range of 3 mg to 15 mg.

In an embodiment the composition comprises a dosage amount in the range of 0.005 mg to 100 mg.

In an embodiment the composition comprises a dosage amount in the range of 0.001 mg to 100 mg.

In an embodiment the composition comprises a dosage amount in the range of 0.0005 mg to 100 mg.

The level of the active agent can be adjusted as required by need for example to suit a certain patient group (e.g. the elderly) or the conditions being treated.

In an embodiment the composition is formulated in a dosage form selected from: oral, transdermal, inhalable, intravenous, rectal dosage, intranasal, intramuscular, or any other parenteral form.

In an embodiment the composition is formulated in a dosage form selected from: oral, transdermal, inhalable, intravenous or rectal dosage It is advantageous to be able to deliver the active agent in different forms, for example to suit a certain patient group (e.g. the elderly) or the conditions being treated.

In an embodiment the composition is formulated in a dosage form selected from: tablet, capsule, granules, powder, free-flowing powder, inhalable powder, aerosol, nebulised, vaping, buccal, sublingual, sublabial, injectable, or suppository dosage form.

In an embodiment the powder is suitable for administration by inhalation via a medicament dispenser selected from a reservoir dry powder inhaler, a unit-dose dry powder inhaler, a pre-metered multi-dose dry powder inhaler, a nasal inhaler or a pressurized metered dose inhaler.

In an embodiment the powder comprises particles, the particles having a median diameter of less than 2000 μm, 1000 μm, 500 μm, 250 μm, 100 μm, 50 μm, or 1 μm.

In an embodiment the powder comprises particles, the particles having a median diameter of greater than 500 μm, 250 μm, 100 μm, 50 μm, 1 μm or 0.5 μm.

In an embodiment the powder comprises particles, and wherein the powder has a particle size distribution of d10=20-60 μm, and/or d50=80-120 μm, and/or d90=130-300 μm.

The nature of the powder can be adjusted to suit need. For example, if being made for nasal inhalation, then the particles may be adjusted to be much finer than if the powder is going to be formulated into a gelatine capsule, or differently again if it is going to be compacted into a tablet.

In an embodiment the compound is in the form of a salt which is amorphous or crystalline.

In an embodiment the salt is in a polymorphic crystalline form.

In an embodiment the salt is a benzoate, fumarate, citrate, acetate, succinate, halide, fluoride, chloride, bromide, iodide, oxalate, or triflate salt, optionally the salt is the chloride, benzoate or fumarate salt.

In an embodiment the salt is formulated into a composition for mucosal delivery. In an embodiment, the salt is a benzoate salt.

For the salt, the dosage amount is the equivalent amount of the free base delivered when the salt is taken. So 100 mg dosage amount may for example correspond to 117 mg of a hydrochloride salt (i.e. both providing the same molar amount of the active substance). The greater mass of the salt needed is due to the larger formula weight of the hydrogen chloride salt. Similarly, for the deuterated or triturated version of the compounds of the invention (also considered within the scope of the invention), a slight increase in mass can be expected due to the increased formula weight of these isotopic compounds.

Amorphous and crystalline substances often show different chemical/physical properties, e.g. improved rate of dissolution in a solvent, or improved thermal stability. Similarly, different polymorphs may also show different and useful chemical/physical properties.

In an embodiment the composition comprises one or more pharmaceutically acceptable carriers or excipients.

In an embodiment the composition comprises one or more of: mucoadhesive enhancer, penetrating enhancer, cationic polymers, cyclodextrins, Tight Junction Modulators, enzyme inhibitors, surfactants, chelators, and polysaccharides.

In an embodiment the composition comprises one or more of: chitosan, chitosan derivatives (such as N,N,N-trimethyl chitosan (TMC), n-propyl-(QuatPropyl), n-butyl-(QuatButyl) and n-hexyl (QuatHexyl)-N,N-dimethyl chitosan, chitosan chloride), β-cyclodextrin, *Clostridium perfringens* enterotoxin, zonula occludens toxin (ZOT), human neutrophil elastase inhibitor (ER143), sodium taurocholate, sodium deoxycholate sodium, sodium lauryl sulphate, glycodeoxycholat, palmitic acid, palmitoleic acid, stearic acid, oleyl acid, oleyl alchohol, capric acid sodium salt, DHA, EPA, dipalmitoyl phophatidyl choline, soybean lecithin, lysophosphatidylcholine, dodecyl maltoside, tetradecyl maltoside, EDTA, lactose, cellulose, and citric acid.

In an embodiment the compound or composition defined herein above for use in a method of treatment of a human or animal subject by therapy.

In an embodiment the method of treatment is a method of treatment of:
conditions caused by dysfunctions of the central nervous system,
conditions caused by dysfunctions of the peripheral nervous system,
conditions benefiting from sleep regulation (such as insomnia),
conditions benefiting from analgesics (such as chronic pain),
migraines,
trigeminal autonomic cephalgias (such as short-lasting unilateral neuralgiform headache with conjunctival injection and tearing (SUNCT), and short-lasting neuralgiform headaches with cranial autonomic symptoms (SUNA)),
conditions benefiting from neurogenesis (such as stroke, traumatic brain injury, Parkinson's dementia),
conditions benefiting from anti-inflammatory treatment,
depression,
anxiety,
substance use disorder,
addictive disorder,
gambling disorder,
eating disorders,
obsessive-compulsive disorders, or
body dysmorphic disorders,
optionally the condition is SUNCT and/or SUNA.

Treatment of the above conditions may be beneficially improved by taking the invention.

In an embodiment the method of treatment is a method of treatment of more than one of the above conditions, for example, the method of treatment may be a method of treatment of depression and anxiety.

In an embodiment the composition is administered one or more times a year.

In an embodiment the composition is administered one or more times a month.

In an embodiment the composition is administered one or more times a week.

In an embodiment the composition is administered one or more times a day.

In an embodiment the composition is administered at such a frequency as to avoid tachyphylaxis.

In an embodiment the composition is administered together with a complementary treatment and/or with a further active agent.

In an embodiment the further active agent is a psychedelic compound, optionally a further tryptamine.

In an embodiment the further active agent is a psychedelic compound, optionally a tryptamine.

In an embodiment the further active agent is psilocybin, psilocin or a prodrug thereof.

In an embodiment the complementary treatment is psychotherapy.

In an embodiment, there is provided a composition comprising a pharmaceutically effective amount of a compound as described herein for use in a method of treatment of treatment resistant depression.

In an embodiment, there is provided a nasal inhalation composition comprising a pharmaceutically effective amount of a compound as described herein for use in a method of treatment of treatment resistant depression.

Treatment of the above conditions may be beneficially improved by taking the invention together with some complementary treatments; also these treatments may occur much less regularly than some other treatments that require daily treatments or even multiple treatments a day.

DETAILED DESCRIPTION OF THE INVENTION

Figure 1:
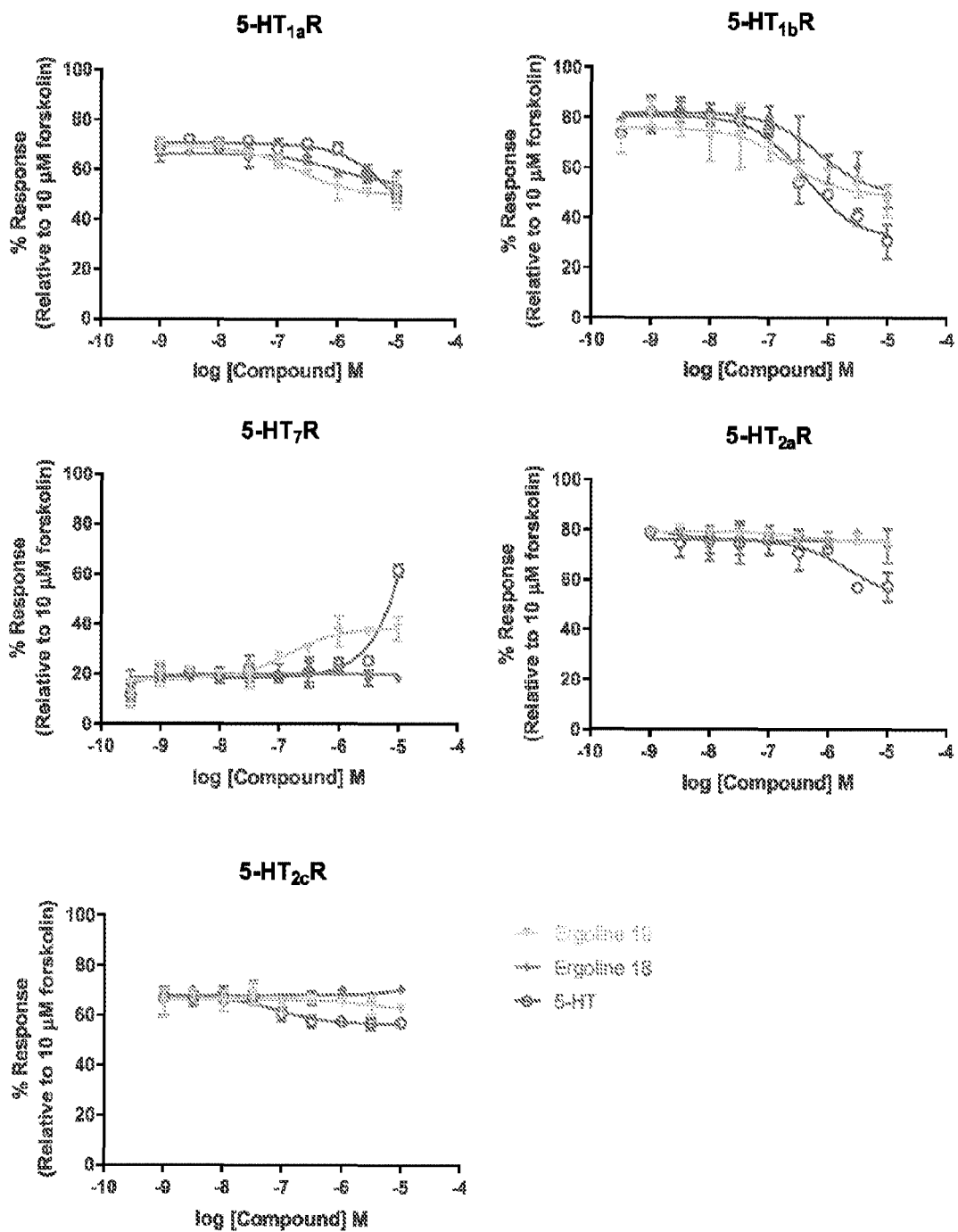
FIG. 1 shows serotonin (1a, 1b, 2a, 2c and 7 receptors) cAMP assay results for compounds 018 and 019.

The crystal structures of the serotonin receptor were retrieved from the Protein Data Bank (www.rcsb.org) [PDB ID: 5TVN and 6WGT for 5-HT2B and 5-HT2A respectively. Both proteins were prepared for docking of candidate ligands. Briefly, hydrogens were added, bond orders were assigned, and loops and side chains were filled. Restrain minimization was performed using Optimized Potentials for Liquid Simulations (OPLS2005) force field until the RMSD reached 0.3 Å from the initial geometry in order to improve steric clashes. Additionally, other possible receptor targets were used and prepared structurally as further indicated below.

Binding Pocket Analysis

Only two crystallographic structures are available from the Protein Data Bank of the 5-HT2A and 5-HT2B receptors in complex with (8alpha)-N,N-diethyl-6-methyl-9,10-didehydroergoline-8-carboxamide which represents an active isoform of LSD. The binding pockets were analysed to determine the interaction between the receptor residues and the ligands structure. Homologies modelling was applied to determine similarities in several receptor/protein targets. Moreover the binding pocket was analysed by intrinsic dynamic Domains (IDD) methodology to further verify the residues on the receptors that most contribute to the activity of the binding site.

Ligands

Initial consideration regarding anti-inflammatory properties, vaso-constriction, vaso-dilation and psychedelic effects were considered.

Upon further analysis the scaffold, lysergic acid amide deprived of the C8 amide group was used. Analysis of key attachment points was implemented and subsequently R-groups were assigned to the initial scaffold. The R-groups were selected from a library of fragments. The compounds were filtered by Lipinski's rule of five (RO5), rapid elimination of swill (REOS) and pan assay interference compounds (PAINS 1, 2, and 3).

The resulting ligand structures were prepared for docking by identifying stereoisomers with protonation states of pH7±2.

Docking

In the binding pocket residues containing hydroxyl and thiol groups were rotated to account for some flexibility of the pocket in the first stage of rigid docking. Subsequently the best compounds were used for flexible docking in order to further simulate a physiological state of the receptors.

Molecular Dynamics Simulation

Simulations for both receptors were implemented on the basis of the top ligand binding scores. All of the simulations were carried out using the MD Desmond package. Available crystal structures were used. The receptor and ligand complexes were set up in an orthorhombic box using a buffer condition of 10 Å. The orientations of the membranes (if available) were from the Orientation of Protein in Membranes (OPM) database. Ions were neutralized for the system, salt was added at a concentration of 0.15 M NaCl, and OPLS 2005 was used for the force field. Long-range electrostatic interactions were calculated with the Ewald method using a cut-off of 9 Å for Van der Waals and Coulomb interactions. The simulation was carried out in an isothermal, isobaric ensemble (NPT) with an initial temperature of 300° K and 1 bar of pressure. The temperature followed the Nose-Hoover method and the pressure was controlled by the Martyna-Tobias-Klein protocol. The simulation was set for 200 ns and trajectories were recorded every 100 ps. The default relaxation protocol for the system was used. Representative structures were extrapolated from the simulation at 0, 100, and 200 ns.

Chemical and Other Pharmacokinetic Properties

The compounds were analysed computationally regarding suitable chemical characteristic and pharmacokinetic parameters and compared across known agonists of mainly the two serotonin receptors (5-HT2A and 2B). Several algorithms were implemented.

Identified Ergoline Analogues

The structures of selected ergoline analogues are shown in the table above and further described below:

Properties of Selected Ergoline Analogues

Various properties of selected ergoline analogues are detailed in the tables below, followed by an explanation of the properties:

| Number | Formula | MW | Heavy atoms |
|---|---|---|---|
| 001 | C11H13N2 | 173.23 | 13 |
| 002 | C20H27N4O2 | 355.45 | 26 |
| 003 | C22H23N4O | 359.44 | 27 |
| 004 | C22H29N4O2 | 381.49 | 28 |
| 005 | C24H27N4O3S | 451.56 | 32 |
| 006 | C21H29N4O2 | 369.48 | 27 |
| 007 | C23H29N4O2 | 393.5 | 29 |
| 008 | C22H28N3O3 | 382.48 | 28 |
| 009 | C23H25N4O3S | 437.53 | 31 |
| 010 | C21H29N4O3S | 417.54 | 29 |
| 011 | C24H25N4O2 | 401.48 | 30 |
| 012 | C22H32N5O3S | 446.59 | 31 |
| 013 | C21H29N4O2 | 369.48 | 27 |
| 014 | C24H31N4O2 | 407.53 | 30 |
| 015 | C25H33N4O2 | 421.56 | 31 |
| 016 | C22H31N4O4S | 447.57 | 31 |
| 017 | C24H36N4O2 | 412.57 | 30 |
| 018 | C24H34N3O | 380.55 | 28 |
| 019 | C19H24N3O | 310.41 | 23 |

| Number | Aromatic heavy atoms | Csp3 | Rotatable bonds |
|---|---|---|---|
| 001 | 9 | 0.27 | 1 |
| 002 | 9 | 0.45 | 6 |
| 003 | 15 | 0.27 | 3 |
| 004 | 9 | 0.5 | 4 |
| 005 | 15 | 0.29 | 5 |

| Number | Aromatic heavy atoms | Csp3 | Rotatable bonds |
|---|---|---|---|
| 006 | 9 | 0.48 | 7 |
| 007 | 9 | 0.52 | 3 |
| 008 | 9 | 0.5 | 4 |
| 009 | 15 | 0.26 | 5 |
| 010 | 9 | 0.48 | 7 |
| 011 | 15 | 0.25 | 5 |
| 012 | 9 | 0.5 | 8 |
| 013 | 9 | 0.48 | 6 |
| 014 | 9 | 0.54 | 4 |
| 015 | 9 | 0.56 | 4 |
| 016 | 9 | 0.5 | 8 |
| 017 | 9 | 0.54 | 8 |
| 018 | 9 | 0.54 | 7 |
| 019 | 9 | 0.42 | 3 |

| Number | H-bond acceptors | H-bond donors | MR |
|---|---|---|---|
| 001 | 0 | 2 | 54.73 |
| 002 | 3 | 4 | 107.22 |
| 003 | 2 | 2 | 112.66 |
| 004 | 3 | 3 | 114.65 |
| 005 | 4 | 2 | 129.16 |
| 006 | 3 | 3 | 111.95 |
| 007 | 3 | 2 | 121.35 |
| 008 | 3 | 2 | 112.93 |
| 009 | 4 | 3 | 124.26 |
| 010 | 4 | 3 | 119.83 |
| 011 | 2 | 3 | 123.06 |
| 012 | 5 | 4 | 127.44 |
| 013 | 3 | 4 | 112.03 |
| 014 | 3 | 2 | 126.16 |
| 015 | 3 | 2 | 130.96 |
| 016 | 5 | 3 | 125.73 |
| 017 | 2 | 3 | 127.73 |
| 018 | 1 | 2 | 122.49 |
| 019 | 1 | 3 | 98.36 |

| Number | TPSA | LOGP | XLOGP3 |
|---|---|---|---|
| 001 | 43.43 | 1.64 | 1.36 |
| 002 | 72.8 | 2.73 | 1.65 |
| 003 | 53.43 | 2.55 | 2.7 |
| 004 | 61.8 | 2.63 | 2.39 |
| 005 | 86.3 | 3.14 | 3.26 |
| 006 | 61.8 | 3.1 | 2.19 |
| 007 | 53.01 | 3.04 | 2.7 |
| 008 | 59 | 2.88 | 2.67 |
| 009 | 95.09 | 2.59 | 3.07 |
| 010 | 95.09 | 2.61 | 1.71 |
| 011 | 69.64 | 2.85 | 3.94 |
| 012 | 107.12 | 2.16 | 1.88 |
| 013 | 72.8 | 2.85 | 2.1 |
| 014 | 53.01 | 3.15 | 3.14 |
| 015 | 53.01 | 3.05 | 3.49 |
| 016 | 104.32 | 2.28 | 2.17 |
| 017 | 54.21 | 3.9 | 3.46 |
| 018 | 40.54 | 3.46 | 4.81 |
| 019 | 49.33 | 2.71 | 2.83 |

| Number | WLOGP | MLOGP | Consensus Log P |
|---|---|---|---|
| 001 | 1.27 | −2.13 | 0.91 |
| 002 | −0.41 | −2.18 | 0.68 |
| 003 | 1.3 | −1.7 | 1.52 |
| 004 | 0.38 | −1.74 | 1.13 |
| 005 | 2.01 | −1.41 | 1.67 |
| 006 | 0.24 | −1.96 | 1.15 |
| 007 | 0.1 | −1.53 | 1.21 |
| 008 | 0.81 | −1.74 | 1.39 |
| 009 | 1.67 | −1.62 | 1.42 |
| 010 | 0.72 | −2.1 | 0.89 |
| 011 | 1.74 | −0.94 | 2.01 |
| 012 | 0.61 | −2.67 | 0.59 |
| 013 | −0.03 | −1.96 | 0.96 |
| 014 | 0.48 | −1.32 | 1.51 |
| 015 | 0.87 | −1.11 | 1.73 |
| 016 | 1.04 | −2.67 | 0.82 |
| 017 | −0.06 | −5 | 1.01 |
| 018 | 2.67 | −0.49 | 2.98 |
| 019 | 0.76 | −1.58 | 1.53 |

| Number | ESOL Log S | ESOL Solubility (mg/ml) | ESOL Solubility (mol/l) |
|---|---|---|---|
| 001 | −2.22 | 1.05 | 0.00607 |
| 002 | −2.94 | 0.405 | 0.00114 |
| 003 | −3.98 | 0.0374 | 0.000104 |
| 004 | −3.68 | 0.0788 | 0.000207 |
| 005 | −4.71 | 0.0088 | 0.0000195 |
| 006 | −3.3 | 0.187 | 0.000507 |
| 007 | −4.01 | 0.0382 | 0.0000972 |
| 008 | −3.87 | 0.0519 | 0.000136 |
| 009 | −4.51 | 0.0134 | 0.0000306 |
| 010 | −3.27 | 0.222 | 0.000532 |
| 011 | −4.85 | 0.00565 | 0.0000141 |
| 012 | −3.48 | 0.148 | 0.000331 |
| 013 | −3.3 | 0.183 | 0.000496 |
| 014 | −4.3 | 0.0203 | 0.0000498 |
| 015 | −4.6 | 0.0105 | 0.0000249 |
| 016 | −3.67 | 0.0959 | 0.000214 |
| 017 | −4.27 | 0.0221 | 0.0000535 |
| 018 | −5.01 | 0.00376 | 0.00000987 |
| 019 | −3.64 | 0.0713 | 0.00023 |

| Number | Solubility Class (ESOL) | (II-method) Log S | Solubility (mg/ml) |
|---|---|---|---|
| 001 | Soluble | −1.87 | 2.31 |
| 002 | Soluble | −2.79 | 0.574 |
| 003 | Soluble | −3.48 | 0.12 |
| 004 | Soluble | −3.33 | 0.179 |
| 005 | Moderately soluble | −4.75 | 0.0081 |
| 006 | Soluble | −3.12 | 0.279 |
| 007 | Moderately soluble | −3.47 | 0.135 |
| 008 | Soluble | −3.56 | 0.105 |
| 009 | Moderately soluble | −4.73 | 0.00808 |
| 010 | Soluble | −3.32 | 0.199 |
| 011 | Moderately soluble | −5.1 | 0.00317 |
| 012 | Soluble | −3.75 | 0.0791 |
| 013 | Soluble | −3.26 | 0.203 |
| 014 | Moderately soluble | −3.92 | 0.0487 |
| 015 | Moderately soluble | −4.29 | 0.0218 |
| 016 | Soluble | −3.99 | 0.0454 |
| 017 | Moderately soluble | −4.28 | 0.0216 |
| 018 | Moderately soluble | −5.39 | 0.00154 |
| 019 | Soluble | −3.52 | 0.0929 |

| Number | Solubility (mol/l) | II method Class | Pgp substrate |
|---|---|---|---|
| 001 | 0.0134 | Very soluble | No |
| 002 | 0.00161 | Soluble | Yes |
| 003 | 0.000335 | Soluble | Yes |
| 004 | 0.000469 | Soluble | Yes |
| 005 | 0.0000179 | Moderately soluble | Yes |
| 006 | 0.000756 | Soluble | Yes |
| 007 | 0.000342 | Soluble | Yes |

-continued

| Number | Solubility (mol/l) | II method Class | Pgp substrate |
|---|---|---|---|
| 008 | 0.000275 | Soluble | Yes |
| 009 | 0.0000185 | Moderately soluble | Yes |
| 010 | 0.000476 | Soluble | Yes |
| 011 | 0.0000079 | Moderately soluble | Yes |
| 012 | 0.000177 | Soluble | Yes |
| 013 | 0.000551 | Soluble | Yes |
| 014 | 0.000119 | Soluble | No |
| 015 | 0.0000518 | Moderately soluble | Yes |
| 016 | 0.000101 | Soluble | Yes |
| 017 | 0.0000525 | Moderately soluble | Yes |
| 018 | 0.00000404 | Moderately soluble | Yes |
| 019 | 0.000299 | Soluble | Yes |

| Number | CYP1A2 inhibitor | CYP2C19 inhibitor | CYP2C9 inhibitor |
|---|---|---|---|
| 001 | Yes | No | No |
| 002 | No | No | No |
| 003 | Yes | No | No |
| 004 | No | No | No |
| 005 | No | No | Yes |
| 006 | No | No | No |
| 007 | No | No | No |
| 008 | No | No | No |
| 009 | No | No | Yes |
| 010 | No | No | No |
| 011 | No | Yes | Yes |
| 012 | No | No | No |
| 013 | No | No | No |
| 014 | No | No | No |
| 015 | No | No | No |
| 016 | No | No | No |
| 017 | No | No | No |
| 018 | No | Yes | Yes |
| 019 | No | No | No |

| Number | CYP2D6 inhibitor | CYP3A4 inhibitor | log Kp (cm/s) |
|---|---|---|---|
| 001 | No | No | −6.39 |
| 002 | No | No | −7.3 |
| 003 | No | No | −6.58 |
| 004 | No | No | −6.93 |
| 005 | No | Yes | −6.74 |
| 006 | No | No | −7 |
| 007 | Yes | No | −6.78 |
| 008 | No | No | −6.74 |
| 009 | No | No | −6.79 |
| 010 | No | No | −7.63 |
| 011 | No | No | −5.95 |
| 012 | No | No | −7.69 |
| 013 | No | No | −7.06 |
| 014 | Yes | No | −6.56 |
| 015 | Yes | No | −6.39 |
| 016 | No | No | −7.49 |
| 017 | No | No | −6.36 |
| 018 | No | No | −5.21 |
| 019 | No | No | −6.18 |

| Number | Lipinski #violations | Ghose violations | Veber violations |
|---|---|---|---|
| 001 | 0 | 0 | 0 |
| 002 | 0 | 1 | 0 |
| 003 | 0 | 0 | 0 |
| 004 | 0 | 0 | 0 |
| 005 | 0 | 0 | 0 |
| 006 | 0 | 0 | 0 |
| 007 | 0 | 0 | 0 |

-continued

| Number | Lipinski #violations | Ghose violations | Veber violations |
|---|---|---|---|
| 008 | 0 | 0 | 0 |
| 009 | 0 | 0 | 0 |
| 010 | 0 | 0 | 0 |
| 011 | 0 | 0 | 0 |
| 012 | 0 | 0 | 0 |
| 013 | 0 | 0 | 0 |
| 014 | 0 | 0 | 0 |
| 015 | 0 | 1 | 0 |
| 016 | 0 | 0 | 0 |
| 017 | 0 | 0 | 0 |
| 018 | 0 | 0 | 0 |
| 019 | 0 | 0 | 0 |

| Number | Egan violations | Muegge violations | Bioavailability Score |
|---|---|---|---|
| 001 | 0 | 1 | 0.55 |
| 002 | 0 | 0 | 0.55 |
| 003 | 0 | 0 | 0.55 |
| 004 | 0 | 0 | 0.55 |
| 005 | 0 | 0 | 0.55 |
| 006 | 0 | 0 | 0.55 |
| 007 | 0 | 0 | 0.55 |
| 008 | 0 | 0 | 0.55 |
| 009 | 0 | 0 | 0.55 |
| 010 | 0 | 0 | 0.55 |
| 011 | 0 | 0 | 0.55 |
| 012 | 0 | 0 | 0.55 |
| 013 | 0 | 0 | 0.55 |
| 014 | 0 | 0 | 0.55 |
| 015 | 0 | 0 | 0.55 |
| 016 | 0 | 0 | 0.55 |
| 017 | 0 | 0 | 0.55 |
| 018 | 0 | 0 | 0.55 |
| 019 | 0 | 0 | 0.55 |

| Number | PAINS alerts | Brenk alerts | Leadlikeness violations |
|---|---|---|---|
| 001 | 0 | 0 | 1 |
| 002 | 0 | 0 | 1 |
| 003 | 0 | 0 | 1 |
| 004 | 0 | 0 | 1 |
| 005 | 0 | 0 | 1 |
| 006 | 0 | 0 | 1 |
| 007 | 0 | 0 | 1 |
| 008 | 0 | 1 | 1 |
| 009 | 0 | 0 | 1 |
| 010 | 0 | 0 | 1 |
| 011 | 0 | 0 | 2 |
| 012 | 0 | 0 | 2 |
| 013 | 0 | 0 | 1 |
| 014 | 0 | 0 | 1 |
| 015 | 0 | 0 | 1 |
| 016 | 0 | 1 | 2 |
| 017 | 0 | 1 | 2 |
| 018 | 0 | 0 | 2 |
| 019 | 0 | 0 | 0 |

| Number | Synthetic Accessibility | Docking scores (Kcal/mol) |
|---|---|---|
| 001 | 2.35 | −8.579 |
| 002 | 4.39 | −13.446 |
| 003 | 4.19 | −12.761 |
| 004 | 4.55 | −12.399 |
| 005 | 4.72 | −12.957 |
| 006 | 4.51 | −12.330 |
| 007 | 5.63 | −12.323 |
| 008 | 4.62 | −12.549 |

-continued

| Number | Synthetic Accessibility | Docking scores (Kcal/mol) |
|---|---|---|
| 009 | 4.59 | −12.506 |
| 010 | 4.64 | −11.908 |
| 011 | 4.43 | −12.275 |
| 012 | 4.84 | −12.818 |
| 013 | 4.51 | −12.370 |
| 014 | 5.76 | −12.593 |
| 015 | 5.89 | −12.395 |
| 016 | 4.92 | −12.366 |
| 017 | 4.98 | −12.362 |
| 018 | 4.62 | −12.146 |
| 019 | 4.09 | −11.855 |

Naming and Strings
  IUPAC name=compound name
  Smile=Smile naming convention of compound
  Formula=Chemical formula compound
Physiochemical Properties
  MW=Molecular weight
  Heavy atoms=Atoms with significantly higher atomic scattering factor than the others present
  Aromatic heavy atoms=As above referring to the ring structures
  Csp3=the ratio of sp3 hybridized carbons over the total carbon count of the molecule (> or equal to 0.25)
  Rotable bonds=Bonds in the molecule that can rotate
  H-Bonds acceptor=Bonds that can accept hydrogen ion
  H-Bonds doner=Bonds that can donate hydrogen ion
  MR=Molecular refractivity
  TPSA=topological polar surface area
Lipophilicity
  LOG P=partition coefficient for ionisable compounds. An approximation implemented by CHARMM version
    c36 (Chemistry at Harvard Macromolecular Mechanics)
  XLOGP=another atomistic method with correction factors from: Cheng, T. et al. Computation of Octanol-Water Partition Coefficients by Guiding an Additive Model with Knowledge. J Chem Inf. Model 47, 2140-2148 (2007).
  WLOGP=is another Log P using the Wildman method described in: Wildman, S. A. & Crippen, G. M. Prediction of Physicochemical Parameters by Atomic Contributions. J. Chem. Inf. Model. 39,868-873 (1999).
  MLOGP=Moriguchi topological method for partition coefficient. Moriguchi, I., Shuichi, H., Liu, Q., Nakagome, I. & Matsushita, Y. Simple Method of Calculating Octanol/Water Partition Coefficient.Chem. Pharm. Bull. 40, 127-130 (1992).
  General Log p=In order to increase the accuracy of the Log P o/W the above methods were used and a general estimation of these values was condensed in "General Log P" column
Solubility
  ESOL Log S=Aqueous solubility by ESOL method: Delaney, J. S. ESOL: Estimating Aqueous Solubility Directly from Molecular Structure. J. Chem. Inf. Model. 44, 1000-1005 (2004)
  ESOL Solubility (mg/ml)=quantification of solubility by SwissADME
  ESOL Solubility (mol/l)=as above
  Solubility class for ESOL method=solubility in aqueous solution
  II methods Log S=Solubility method based on: Ali, J., Camilleri, P., Brown, M. B., Hutt, A. J. & Kirton, S. B. Revisiting the general solubility equation: in silico prediction of aqueous solubility incorporating the effect of topographical polar surface area. J. Chem. Inf. Model. 52, 420-428 (2012).
Pharmacokinetics
  Pgp substrate=P glycoprotein, this describes if the compound is a substrate of glycoprotein associated with the permeability of biological membranes.
  The below subfamilies of the cytochrome P450 determine drug elimination and metabolism in association with Pgp data: CYP1A2 inhibitor, CYP2C19 inhibitor, CYP2C9 inhibitor, CYP2D6 inhibitor, CYP3A4 inhibitor,
Drug-Likeness
  Lipinski violations
  Ghose violations
  Veber violations
  Egan violations
  Muegge violations
Bioavailability Score (The Abbot Bioavailability Score)
Synthesis
  "PAINS (Pan-assay interference compounds)=Baell, J. B. & Holloway, G. A. New substructure filters for removal of pan assay interference compounds (PAINS) from screening libraries and for their exclusion in bioassays. J. Med. Chem. 53, 2719-2740 (2010)."
  "Brenk alerts=Brenk, R. et al. Lessons learnt from assembling screening libraries for drug discovery for neglected diseases. ChemMedChem 3,435-444 (2008)."
  "Lead likeness violations=based on: Teague, S., Davis, A., Leeson, P. & Oprea, T. The Design of Lead like Combinatorial Libraries. Angew. Chem. Int. Ed. Engl. 38,3743-3748 (1999)."
  "Synthetic Accessibility=based on two papers: Fukunishi, Y., Kurosawa, T., Mikami, Y. & Nakamura, H. Prediction of synthetic accessibility based on commercially available compound databases. J Chem Inf Model 54, 3259-3267 (2014).
  Ertl, P. & Schuffenhauer, A. Estimation of synthetic accessibility score of drug-like molecules based on molecular complexity and fragment contributions. J. Cheminform. 1, 8 (2009). From 1 to 10 with 1 easy and 10 complex"
Docking Scores (Kcal/mol)
  Scores are reported for docking to the target, the highest negative number indicates a better binding pose of the ligand in the receptor (5-HT2A) (similar scores are related to the 5-HT2B).

| Abbreviations | |
|---|---|
| 5-HT# = 5-hydroxytryptamine receptor # | HH1R = Histamine H1 receptor |
| A#AR = Alpha-# adrenergic receptor | M. Rec = Membrane receptor |
| B#AR = Beta-# adrenergic receptor | MAPTau = Microtubule-associated protein tau |
| CP450# = Cytochrome P450 # | MBLP# = Muscleblind-like protein # |
| CXCCRT3 = C-X-C chemokine receptor type 3 | Na-Dep = Sodium-dependent Trans. = Transporter |
| D(#)DR = D(#)DR | |
| D(#)DR = D(#) dopamine receptor | Unc = Unclassified |
| Enz = Enzyme | where # = a number |

Compound/Target Data
Further Information Regarding Targets Screened
  The table below details the range of targets that selected ergoline analogues were screened against and the results.

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| 001 | 5HTR2A | P28223 | HTR2A | 224 | No | 1 | 76 | 193 | M. Rec |
|  | 5HTR2C | P28335 | HTR2C | 225 | No | 1 | 71 | 151 | M. Rec |
|  | 5HTR2B | P41595 | HTR2B | 1833 | No | 1 | 71 | 151 | M. Rec |
|  | 5HTR1A | P08908 | HTR1A | 214 | Yes | 0.74 | 12 | 528 | M. Rec |
|  | 5HTR1D | P28221 | HTR1D | 1983 | No | 0.74 | 17 | 444 | M. Rec |
|  | 5HTR1B | P28222 | HTR1B | 1898 | No | 0.74 | 19 | 542 | M. Rec |
|  | 5HTR1E | P28566 | HTR1E | 2182 | Yes | 0.74 | 10 | 425 | M. Rec |
|  | 5HTR1F | P30939 | HTR1F | 1805 | Yes | 0.74 | 10 | 425 | M. Rec |
|  | 5HTR6 | P50406 | HTR6 | 3371 | No | 0.74 | 6 | 184 | M. Rec |
|  | MBLP#1 | Q9NR56 | MBNL1 | 1293317 | No | 0.74 | 1 | 19 | Unc |
|  | MBLP#2 | Q5VZF2 | MBNL2 |  | Yes | 0.74 | 1 | 19 | Unc |
|  | MBLP#3 | Q9NUK0 | MBNL3 |  | Yes | 0.74 | 1 | 19 | Unc |
|  | Na-Dep noradrenaline Trans. | P23975 | SLC6A2 | 222 | Yes | 0.64 | 18 | 194 | Trans. |
|  | Na-Dep serotonin Trans. | P31645 | SLC6A4 | 228 | No | 0.64 | 35 | 262 | Trans. |
|  | Na-Dep dopamine Trans. | Q01959 | SLC6A3 | 238 | No | 0.64 | 18 | 194 | Trans. |
| 002 | D(2)DR | P14416 | DRD2 | 217 | No | 0.88 | 383 | 93 | M. Rec |
|  | D(1A)DR | P21728 | DRD1 | 2056 | No | 0.88 | 33 | 20 | M. Rec |
|  | D(4)DR | P21917 | DRD4 | 219 | No | 0.88 | 182 | 17 | M. Rec |
|  | D(1B)DR | P21918 | DRD5 | 1850 | No | 0.88 | 27 | 20 | M. Rec |
|  | 5HTR1D | P28221 | HTR1D | 1983 | No | 0.88 | 75 | 86 | M. Rec |
|  | 5HTR1B | P28222 | HTR1B | 1898 | Yes | 0.88 | 225 | 111 | M. Rec |
|  | 5HTR2A | P28223 | HTR2A | 224 | No | 0.88 | 166 | 34 | M. Rec |
|  | 5HTR2C | P28335 | HTR2C | 225 | No | 0.88 | 111 | 23 | M. Rec |
|  | D(3)DR | P35462 | DRD3 | 234 | No | 0.88 | 217 | 40 | M. Rec |
|  | 5HTR2B | P41595 | HTR2B | 1833 | No | 0.88 | 111 | 23 | M. Rec |
|  | 5HTR6 | P50406 | HTR6 | 3371 | No | 0.88 | 33 | 52 | M. Rec |
|  | B2AR | P07550 | ADRB2 | 210 | No | 0.87 | 439 | 7 | M. Rec |
|  | B1AR | P08588 | ADRB1 | 213 | No | 0.87 | 444 | 7 | M. Rec |
|  | B3AR | P13945 | ADRB3 | 246 | Yes | 0.87 | 427 | 7 | M. Rec |
|  | A2aAR | P08913 | ADRA2A | 1867 | No | 0.87 | 39 | 10 | M. Rec |
| 003 | D(2)DR | P14416 | DRD2 | 217 | No | 0.89 | 2724 | 112 | M. Rec |
|  | D(3)DR | P35462 | DRD3 | 234 | No | 0.89 | 1579 | 46 | M. Rec |
|  | 5HTR1A | P08908 | HTR1A | 214 | No | 0.87 | 1288 | 107 | M. Rec |
|  | 5HTR1B | P28222 | HTR1B | 1898 | Yes | 0.87 | 1358 | 117 | M. Rec |
|  | D(1A)DR | P21728 | DRD1 | 2056 | No | 0.87 | 252 | 20 | M. Rec |
|  | D(1B)DR | P21918 | DRD5 | 1850 | No | 0.87 | 181 | 20 | M. Rec |
|  | 5HTR1D | P28221 | HTR1D | 1983 | No | 0.86 | 549 | 86 | M. Rec |
|  | 5HTR1E | P28566 | HTR1E | 2182 | No | 0.86 | 442 | 72 | M. Rec |
|  | 5HTR1F | P30939 | HTR1F | 1805 | No | 0.86 | 442 | 72 | M. Rec |
|  | 5HTR6 | P50406 | HTR6 | 3371 | No | 0.85 | 484 | 54 | M. Rec |
|  | D(4)DR | P21917 | DRD4 | 219 | No | 0.85 | 1030 | 17 | M. Rec |
|  | 5HTR2A | P28223 | HTR2A | 224 | No | 0.85 | 1067 | 35 | M. Rec |
|  | 5HTR7 | P34969 | HTR7 | 3155 | No | 0.85 | 411 | 19 | M. Rec |
|  | 5HTR2C | P28335 | HTR2C | 225 | No | 0.85 | 636 | 24 | M. Rec |
|  | 5HTR2B | P41595 | HTR2B | 1833 | No | 0.85 | 636 | 24 | M. Rec |
| 004 | 5HTR7 | P34969 | HTR7 | 3155 | No | 0.84 | 52 | 14 | M. Rec |
|  | 5HTR5A | P47898 | HTR5A | 3426 | No | 0.84 | 8 | 9 | M. Rec |
|  | 5HTR6 | P50406 | HTR6 | 3371 | No | 0.84 | 65 | 39 | M. Rec |
|  | D(2)DR | P14416 | DRD2 | 217 | No | 0.84 | 621 | 82 | M. Rec |
|  | D(1A)DR | P21728 | DRD1 | 2056 | No | 0.84 | 48 | 19 | M. Rec |
|  | D(4)DR | P21917 | DRD4 | 219 | No | 0.84 | 311 | 16 | M. Rec |
|  | D(1B)DR | P21918 | DRD5 | 1850 | No | 0.84 | 40 | 19 | M. Rec |
|  | 5HTR1D | P28221 | HTR1D | 1983 | No | 0.84 | 132 | 84 | M. Rec |
|  | 5HTR1B | P28222 | HTR1B | 1898 | Yes | 0.84 | 342 | 99 | M. Rec |
|  | 5HTR2A | P28223 | HTR2A | 224 | No | 0.84 | 285 | 32 | M. Rec |
|  | 5HTR2C | P28335 | HTR2C | 225 | No | 0.84 | 217 | 21 | M. Rec |
|  | D(3)DR | P35462 | DRD3 | 234 | No | 0.84 | 383 | 37 | M. Rec |
|  | 5HTR2B | P41595 | HTR2B | 1833 | No | 0.84 | 217 | 21 | M. Rec |
|  | 5HTR1A | P08908 | HTR1A | 214 | No | 0.83 | 333 | 89 | M. Rec |
|  | A2aAR | P08913 | ADRA2A | 1867 | No | 0.81 | 75 | 9 | M. Rec |
| 005 | D(2)DR | P14416 | DRD2 | 217 | No | 0.77 | 1437 | 60 | M. Rec |
|  | D(4)DR | P21917 | DRD4 | 219 | No | 0.77 | 549 | 18 | M. Rec |
|  | D(3)DR | P35462 | DRD3 | 234 | No | 0.77 | 850 | 37 | M. Rec |
|  | 5HTR1A | P08908 | HTR1A | 214 | No | 0.75 | 791 | 56 | M. Rec |
|  | 5HTR1D | P28221 | HTR1D | 1983 | No | 0.75 | 305 | 52 | M. Rec |
|  | 5HTR1B | P28222 | HTR1B | 1898 | No | 0.75 | 847 | 61 | M. Rec |
|  | 5HTR2A | P28223 | HTR2A | 224 | No | 0.75 | 599 | 27 | M. Rec |
|  | 5HTR1E | P28566 | HTR1E | 2182 | No | 0.75 | 236 | 45 | M. Rec |
|  | 5HTR1F | P30939 | HTR1F | 1805 | No | 0.75 | 236 | 45 | M. Rec |
|  | 5HTR7 | P34969 | HTR7 | 3155 | No | 0.75 | 255 | 12 | M. Rec |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| | 5HTR5A | P47898 | HTR5A | 3426 | No | 0.75 | 45 | 9 | M. Rec |
| | 5HTR6 | P50406 | HTR6 | 3371 | No | 0.75 | 417 | 87 | M. Rec |
| | 5HTR2C | P28335 | HTR2C | 225 | No | 0.75 | 368 | 15 | M. Rec |
| | 5HTR2B | P41595 | HTR2B | 1833 | No | 0.75 | 368 | 15 | M. Rec |
| | B2AR | P07550 | ADRB2 | 210 | No | 0.73 | 19 | 7 | M. Rec |
| 006 | 5HT1A | P08908 | HTR1A | 214 | No | 0.88 | 338 | 102 | M. Rec |
| | 5HTR1B | P28222 | HTR1B | 1898 | Yes | 0.88 | 346 | 112 | M. Rec |
| | 5HTR2A | P28223 | HTR2A | 224 | No | 0.86 | 299 | 33 | M. Rec |
| | 5HTR2C | P28335 | HTR2C | 225 | No | 0.86 | 230 | 22 | M. Rec |
| | 5HTR2B | P41595 | HTR2B | 1833 | No | 0.86 | 230 | 22 | M. Rec |
| | 5HTR6 | P50406 | HTR6 | 3371 | No | 0.86 | 69 | 48 | M. Rec |
| | D(2)DR | P14416 | DRD2 | 217 | No | 0.86 | 610 | 92 | M. Rec |
| | D(1A)DR | P21728 | DRD1 | 2056 | No | 0.86 | 46 | 20 | M. Rec |
| | D(4)DR | P21917 | DRD4 | 219 | No | 0.86 | 315 | 17 | M. Rec |
| | D(1B)DR | P21918 | DRD5 | 1850 | No | 0.86 | 40 | 20 | M. Rec |
| | 5HTR1D | P28221 | HTR1D | 1983 | No | 0.86 | 131 | 85 | M. Rec |
| | 5HTR7 | P34969 | HTR7 | 3155 | No | 0.86 | 56 | 16 | M. Rec |
| | D(3)DR | P35462 | DRD3 | 234 | No | 0.86 | 377 | 38 | M. Rec |
| | B2AR | P07550 | ADRB2 | 210 | No | 0.85 | 536 | 7 | M. Rec |
| | B1AR | P08588 | ADRB1 | 213 | No | 0.85 | 539 | 7 | M. Rec |
| 007 | D(2)DR | P14416 | DRD2 | 217 | No | 0.77 | 621 | 74 | M. Rec |
| | D(1A)DR | P21728 | DRD1 | 2056 | No | 0.77 | 50 | 18 | M. Rec |
| | D(4)DR | P21917 | DRD4 | 219 | Yes | 0.77 | 334 | 15 | M. Rec |
| | D(3)DR | P35462 | DRD3 | 234 | No | 0.77 | 400 | 36 | M. Rec |
| | 5HTR6 | P50406 | HTR6 | 3371 | No | 0.75 | 65 | 26 | M. Rec |
| | 5HTR2A | P28223 | HTR2A | 224 | No | 0.75 | 309 | 26 | M. Rec |
| | D(1B)DR | P21918 | DRD5 | 1850 | No | 0.74 | 44 | 18 | M. Rec |
| | 5HTR2C | P28335 | HTR2C | 225 | No | 0.74 | 237 | 15 | M. Rec |
| | 5HTR2B | P41595 | HTR2B | 1833 | No | 0.74 | 237 | 15 | M. Rec |
| | A2aAR | P08913 | ADRA2A | 1867 | No | 0.72 | 84 | 8 | M. Rec |
| | A2BAR | P18089 | ADRA2B | 1942 | No | 0.72 | 84 | 8 | M. Rec |
| | A2CAR | P18825 | ADRA2C | 1916 | Yes | 0.72 | 84 | 8 | M. Rec |
| | MAPTau | P10636 | MAPT | 1293224 | No | 0.72 | 307 | 9 | Unc |
| | HH1R | P35367 | HRH1 | 231 | No | 0.72 | 94 | 5 | M. Rec |
| | 5HTR1D | P28221 | HTR1D | 1983 | No | 0.72 | 116 | 73 | M. Rec |
| 008 | D(2)DR | P14416 | DRD2 | 217 | No | 0.79 | 539 | 65 | M. Rec |
| | 5HTR1A | P08908 | HTR1A | 214 | No | 0.77 | 301 | 76 | M. Rec |
| | 5HTR1B | P28222 | HTR1B | 1898 | Yes | 0.77 | 310 | 86 | M. Rec |
| | D(4)DR | P21917 | DRD4 | 219 | No | 0.75 | 274 | 15 | M. Rec |
| | D(3)DR | P35462 | DRD3 | 234 | No | 0.75 | 324 | 36 | M. Rec |
| | 5HTR2A | P28223 | HTR2A | 224 | No | 0.75 | 269 | 29 | M. Rec |
| | 5HTR2C | P28335 | HTR2C | 225 | No | 0.75 | 205 | 18 | M. Rec |
| | HH1R | P35367 | HRH1 | 231 | No | 0.75 | 99 | 5 | M. Rec |
| | 5HTR2B | P41595 | HTR2B | 1833 | No | 0.75 | 205 | 18 | M. Rec |
| | B2AR | P07550 | ADRB2 | 210 | No | 0.75 | 473 | 7 | M. Rec |
| | B1AR | P08588 | ADRB1 | 213 | No | 0.75 | 475 | 7 | M. Rec |
| | B3AR | P13945 | ADRB3 | 246 | No | 0.75 | 455 | 7 | M. Rec |
| | D(1A)DR | P21728 | DRD1 | 2056 | No | 0.75 | 38 | 18 | M. Rec |
| | D(1B)DR | P21918 | DRD5 | 1850 | No | 0.75 | 33 | 18 | M. Rec |
| | 5HTR1D | P28221 | HTR1D | 1983 | No | 0.75 | 100 | 77 | M. Rec |
| 009 | 5HTR2A | P28223 | HTR2A | 224 | No | 0.83 | 773 | 28 | M. Rec |
| | D(2)DR | P14416 | DRD2 | 217 | No | 0.83 | 1942 | 74 | M. Rec |
| | D(4)DR | P21917 | DRD4 | 219 | No | 0.83 | 721 | 18 | M. Rec |
| | D(3)DR | P35462 | DRD3 | 234 | No | 0.83 | 1145 | 38 | M. Rec |
| | 5HTR1A | P08908 | HTR1A | 214 | No | 0.8 | 1076 | 68 | M. Rec |
| | 5HTR1B | P28222 | HTR1B | 1898 | Yes | 0.8 | 1130 | 76 | M. Rec |
| | 5HTR1D | P28221 | HTR1D | 1983 | No | 0.8 | 407 | 65 | M. Rec |
| | 5HTR2C | P28335 | HTR2C | 225 | No | 0.8 | 478 | 16 | M. Rec |
| | 5HTR1E | P28566 | HTR1E | 2182 | No | 0.8 | 335 | 54 | M. Rec |
| | 5HTR1F | P30939 | HTR1F | 1805 | No | 0.8 | 335 | 54 | M. Rec |
| | 5HTR7 | P34969 | HTR7 | 3155 | No | 0.8 | 310 | 14 | M. Rec |
| | 5HTR2B | P41595 | HTR2B | 1833 | No | 0.8 | 478 | 16 | M. Rec |
| | 5HTR6 | P50406 | HTR6 | 3371 | No | 0.8 | 568 | 69 | M. Rec |
| | 5HTR5A | P47898 | HTR5A | 3426 | No | 0.8 | 52 | 10 | M. Rec |
| | D(1A)DR | P21728 | DRD1 | 2056 | No | 0.78 | 191 | 18 | M. Rec |
| 010 | 5HTR6 | P50406 | HTR6 | 3371 | No | 0.82 | 383 | 55 | M. Rec |
| | D(4)DR | P21917 | DRD4 | 219 | No | 0.82 | 950 | 16 | M. Rec |
| | D(2)DR | P14416 | DRD2 | 217 | No | 0.8 | 2423 | 73 | M. Rec |
| | 5HTR1D | P28221 | HTR1D | 1983 | No | 0.8 | 487 | 74 | M. Rec |
| | 5HTR1B | P28222 | HTR1B | 1898 | Yes | 0.8 | 1283 | 86 | M. Rec |
| | 5HTR2A | P28223 | HTR2A | 224 | No | 0.8 | 959 | 32 | M. Rec |
| | 5HTR7 | P34969 | HTR7 | 3155 | No | 0.8 | 465 | 14 | M. Rec |
| | 5HTR1A | P08908 | HTR1A | 214 | No | 0.8 | 1246 | 76 | M. Rec |
| | D(1A)DR | P21728 | DRD1 | 2056 | No | 0.8 | 189 | 19 | M. Rec |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| | D(1B)DR | P21918 | DRD5 | 1850 | No | 0.8 | 145 | 19 | M. Rec |
| | 5HTR2C | P28335 | HTR2C | 225 | No | 0.8 | 575 | 21 | M. Rec |
| | D(3)DR | P35462 | DRD3 | 234 | No | 0.8 | 1516 | 37 | M. Rec |
| | 5HTR2B | P41595 | HTR2B | 1833 | No | 0.8 | 575 | 21 | M. Rec |
| | 5HTR1E | P28566 | HTR1E | 2182 | No | 0.79 | 419 | 60 | M. Rec |
| | 5HTR1F | P30939 | HTR1F | 1805 | Yes | 0.79 | 419 | 60 | M. Rec |
| 011 | 5HTR1A | P08908 | HTR1A | 214 | No | 0.91 | 1137 | 78 | M. Rec |
| | 5HTR1B | P28222 | HTR1B | 1898 | Yes | 0.91 | 1194 | 88 | M. Rec |
| | 5HTR6 | P50406 | HTR6 | 3371 | No | 0.9 | 361 | 44 | M. Rec |
| | D(2)DR | P14416 | DRD2 | 217 | No | 0.9 | 2285 | 86 | M. Rec |
| | D(3)DR | P35462 | DRD3 | 234 | No | 0.9 | 1325 | 36 | M. Rec |
| | D(4)DR | P21917 | DRD4 | 219 | No | 0.89 | 823 | 16 | M. Rec |
| | 5HTR2A | P28223 | HTR2A | 224 | No | 0.89 | 803 | 30 | M. Rec |
| | D(1A)DR | P21728 | DRD1 | 2056 | No | 0.89 | 239 | 19 | M. Rec |
| | D(1B)DR | P21918 | DRD5 | 1850 | No | 0.89 | 181 | 19 | M. Rec |
| | 5HTR2C | P28335 | HTR2C | 225 | Yes | 0.88 | 469 | 19 | M. Rec |
| | 5HTR2B | P41595 | HTR2B | 1833 | No | 0.88 | 469 | 19 | M. Rec |
| | A2aAR | P08913 | ADRA2A | 1867 | No | 0.88 | 54 | 9 | M. Rec |
| | A2BAR | P18089 | ADRA2B | 1942 | Yes | 0.88 | 55 | 9 | M. Rec |
| | A2CAR | P18825 | ADRA2C | 1916 | No | 0.88 | 54 | 9 | M. Rec |
| | CXCCRT3 | P49682 | CXCR3 | 4441 | No | 0.86 | 90 | 63 | M. Rec |
| 012 | 5HTR6 | P50406 | HTR6 | 3371 | No | 0.84 | 483 | 39 | M. Rec |
| | 5HTR1A | P08908 | HTR1A | 214 | No | 0.83 | 1292 | 68 | M. Rec |
| | 5HTR1D | P28221 | HTR1D | 1983 | No | 0.83 | 522 | 69 | M. Rec |
| | 5HTR1B | P28222 | HTR1B | 1898 | No | 0.83 | 1337 | 77 | M. Rec |
| | 5HTR1E | P28566 | HTR1E | 2182 | No | 0.83 | 441 | 57 | M. Rec |
| | 5HTR1F | P30939 | HTR1F | 1805 | Yes | 0.83 | 441 | 57 | M. Rec |
| | 5HTR2A | P28223 | HTR2A | 224 | No | 0.8 | 936 | 29 | M. Rec |
| | D(2)DR | P14416 | DRD2 | 217 | No | 0.78 | 2317 | 74 | M. Rec |
| | D(4)DR | P21917 | DRD4 | 219 | No | 0.78 | 909 | 15 | M. Rec |
| | D(3)DR | P35462 | DRD3 | 234 | No | 0.78 | 1434 | 36 | M. Rec |
| | 5HTR2C | P28335 | HTR2C | 225 | No | 0.78 | 563 | 18 | M. Rec |
| | 5HTR7 | P34969 | HTR7 | 3155 | No | 0.78 | 472 | 12 | M. Rec |
| | 5HTR2B | P41595 | HTR2B | 1833 | No | 0.78 | 563 | 18 | M. Rec |
| | D(1A)DR | P21728 | DRD1 | 2056 | No | 0.78 | 173 | 18 | M. Rec |
| | D(1B)DR | P21918 | DRD5 | 1850 | No | 0.78 | 128 | 18 | M. Rec |
| 013 | D(2)DR | P14416 | DRD2 | 217 | No | 0.9 | 430 | 95 | M. Rec |
| | D(1A)DR | P21728 | DRD1 | 2056 | No | 0.9 | 36 | 20 | M. Rec |
| | D(4)DR | P21917 | DRD4 | 219 | No | 0.9 | 235 | 17 | M. Rec |
| | D(1B)DR | P21918 | DRD5 | 1850 | No | 0.9 | 32 | 20 | M. Rec |
| | 5HTR1D | P28221 | HTR1D | 1983 | No | 0.9 | 90 | 84 | M. Rec |
| | 5HTR1B | P28222 | HTR1B | 1898 | Yes | 0.9 | 274 | 111 | M. Rec |
| | 5HTR2A | P28223 | HTR2A | 224 | No | 0.9 | 207 | 33 | M. Rec |
| | 5HTR2C | P28335 | HTR2C | 225 | No | 0.9 | 150 | 22 | M. Rec |
| | D(3)DR | P35462 | DRD3 | 234 | No | 0.9 | 262 | 38 | M. Rec |
| | 5HTR2B | P41595 | HTR2B | 1833 | No | 0.9 | 150 | 22 | M. Rec |
| | 5HTR6 | P50406 | HTR6 | 3371 | No | 0.9 | 46 | 57 | M. Rec |
| | 5HTR7 | P34969 | HTR7 | 3155 | No | 0.89 | 29 | 16 | M. Rec |
| | 5HTR1A | P08908 | HTR1A | 214 | No | 0.88 | 267 | 101 | M. Rec |
| | A2aAR | P08913 | ADRA2A | 1867 | No | 0.88 | 52 | 10 | M. Rec |
| | A2BAR | P18089 | ADRA2B | 1942 | No | 0.88 | 52 | 10 | M. Rec |
| 014 | 5HTR1B | P28222 | HTR1B | 1898 | Yes | 0.75 | 365 | 78 | M. Rec |
| | D(2)DR | P14416 | DRD2 | 217 | No | 0.74 | 631 | 57 | M. Rec |
| | D(1A)DR | P21728 | DRD1 | 2056 | No | 0.74 | 53 | 18 | M. Rec |
| | D(4)DR | P21917 | DRD4 | 219 | Yes | 0.74 | 350 | 15 | M. Rec |
| | D(3)DR | P35462 | DRD3 | 234 | No | 0.74 | 413 | 33 | M. Rec |
| | 5HTR2A | P28223 | HTR2A | 224 | No | 0.74 | 333 | 25 | M. Rec |
| | 5HTR2C | P28335 | HTR2C | 225 | No | 0.74 | 259 | 14 | M. Rec |
| | 5HTR2B | P41595 | HTR2B | 1833 | No | 0.74 | 259 | 14 | M. Rec |
| | 5HTR6 | P50406 | HTR6 | 3371 | No | 0.72 | 78 | 19 | M. Rec |
| | 5HTR1D | P28221 | HTR1D | 1983 | No | 0.72 | 118 | 61 | M. Rec |
| | 5HTR1A | P08908 | HTR1A | 214 | No | 0.72 | 358 | 73 | M. Rec |
| | CP4502D6 | P10635 | CYP2D6 | 289 | No | 0.72 | 23 | 2 | Enz |
| | CP4502J2 | P51589 | CYP2J2 | 3491 | No | 0.72 | 23 | 2 | Enz |
| | A2aAR | P08913 | ADRA2A | 1867 | No | 0.72 | 91 | 8 | M. Rec |
| | MAPTau | P10636 | MAPT | 1293224 | No | 0.72 | 348 | 8 | Unc |
| 015 | CP4502D6 | P10635 | CYP2D6 | 289 | No | 0.78 | 22 | 2 | Enz |
| | CP4502J2 | P51589 | CYP2J2 | 3491 | No | 0.78 | 22 | 2 | Enz |
| | MAPTau | P10636 | MAPT | 1293224 | No | 0.77 | 268 | 9 | Unc |
| | D(4)DR | P21917 | DRD4 | 219 | No | 0.77 | 311 | 15 | M. Rec |
| | 5HTR2A | P28223 | HTR2A | 224 | No | 0.77 | 314 | 25 | M. Rec |
| | 5HTR2C | P28335 | HTR2C | 225 | No | 0.77 | 249 | 14 | M. Rec |
| | 5HTR2B | P41595 | HTR2B | 1833 | No | 0.77 | 249 | 14 | M. Rec |
| | MBLP#1 | Q9NR56 | MBNL1 | 1293317 | No | 0.75 | 227 | 3 | Unc |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| | MBLP#2 | Q5VZF2 | MBNL2 | | Yes | 0.75 | 227 | 3 | Unc |
| | MBLP#3 | Q9NUK0 | MBNL3 | | Yes | 0.75 | 227 | 3 | Unc |
| | 5HTR6 | P50406 | HTR6 | 3371 | No | 0.75 | 82 | 19 | M. Rec |
| | D(2)DR | P14416 | DRD2 | 217 | No | 0.73 | 564 | 57 | M. Rec |
| | D(1A)DR | P21728 | DRD1 | 2056 | No | 0.73 | 49 | 18 | M. Rec |
| | D(1B)DR | P21918 | DRD5 | 1850 | Yes | 0.73 | 42 | 18 | M. Rec |
| | 5HTR1D | P28221 | HTR1D | 1983 | No | 0.73 | 113 | 58 | M. Rec |
| 016 | 5HTR1A | P08908 | HTR1A | 214 | No | 0.8 | 1056 | 43 | M. Rec |
| | 5HTR1D | P28221 | HTR1D | 1983 | No | 0.8 | 385 | 45 | M. Rec |
| | 5HTR1B | P28222 | HTR1B | 1898 | No | 0.8 | 1103 | 50 | M. Rec |
| | 5HTR1E | P28566 | HTR1E | 2182 | No | 0.8 | 314 | 36 | M. Rec |
| | 5HTR1F | P30939 | HTR1F | 1805 | Yes | 0.8 | 314 | 36 | M. Rec |
| | D(2)DR | P14416 | DRD2 | 217 | No | 0.78 | 2111 | 59 | M. Rec |
| | D(1A)DR | P21728 | DRD1 | 2056 | Yes | 0.78 | 129 | 18 | M. Rec |
| | D(4)DR | P21917 | DRD4 | 219 | No | 0.78 | 718 | 15 | M. Rec |
| | D(3)DR | P35462 | DRD3 | 234 | No | 0.78 | 1173 | 34 | M. Rec |
| | 5HTR2A | P28223 | HTR2A | 224 | No | 0.77 | 840 | 26 | M. Rec |
| | 5HTR7 | P34969 | HTR7 | 3155 | No | 0.75 | 367 | 10 | M. Rec |
| | 5HTR2C | P28335 | HTR2C | 225 | No | 0.71 | 515 | 15 | M. Rec |
| | 5HTR2B | P41595 | HTR2B | 1833 | No | 0.71 | 515 | 15 | M. Rec |
| | 5HTR6 | P50406 | HTR6 | 3371 | No | 0.71 | 287 | 35 | M. Rec |
| | D(1B)DR | P21918 | DRD5 | 1850 | No | 0.69 | 83 | 18 | M. Rec |
| 017 | 5HTR1A | P08908 | HTR1A | 214 | No | 0.8 | 735 | 88 | M. Rec |
| | 5HTR1B | P28222 | HTR1B | 1898 | Yes | 0.8 | 781 | 98 | M. Rec |
| | D(2)DR | P14416 | DRD2 | 217 | No | 0.77 | 1408 | 76 | M. Rec |
| | 5HTR2A | P28223 | HTR2A | 224 | No | 0.77 | 563 | 30 | M. Rec |
| | 5HTR2C | P28335 | HTR2C | 225 | No | 0.77 | 342 | 19 | M. Rec |
| | D(3)DR | P35462 | DRD3 | 234 | No | 0.77 | 752 | 37 | M. Rec |
| | 5HTR2B | P41595 | HTR2B | 1833 | No | 0.77 | 342 | 19 | M. Rec |
| | 5HTR6 | P50406 | HTR6 | 3371 | No | 0.75 | 256 | 37 | M. Rec |
| | MAPTau | P10636 | MAPT | 1293224 | No | 0.75 | 398 | 12 | Unc |
| | D(4)DR | P21917 | DRD4 | 219 | No | 0.75 | 469 | 16 | M. Rec |
| | 5HTR1D | P28221 | HTR1D | 1983 | No | 0.75 | 263 | 84 | M. Rec |
| | 5HTR7 | P34969 | HTR7 | 3155 | No | 0.75 | 240 | 13 | M. Rec |
| | 5HTR5A | P47898 | HTR5A | 3426 | No | 0.75 | 23 | 9 | M. Rec |
| | 5HTR1E | P28566 | HTR1E | 2182 | No | 0.75 | 203 | 70 | M. Rec |
| | 5HTR1F | P30939 | HTR1F | 1805 | Yes | 0.75 | 203 | 70 | M. Rec |
| 018 | 5HTR2A | P28223 | HTR2A | 224 | Yes | 0.94 | 384 | 39 | M. Rec |
| | D(2)DR | P14416 | DRD2 | 217 | No | 0.94 | 823 | 160 | M. Rec |
| | D(4)DR | P21917 | DRD4 | 219 | No | 0.94 | 340 | 23 | M. Rec |
| | D(3)DR | P35462 | DRD3 | 234 | No | 0.94 | 488 | 80 | M. Rec |
| | D(1A)DR | P21728 | DRD1 | 2056 | No | 0.93 | 77 | 20 | M. Rec |
| | D(1B)DR | P21918 | DRD5 | 1850 | No | 0.93 | 60 | 20 | M. Rec |
| | 5HTR2C | P28335 | HTR2C | 225 | No | 0.92 | 208 | 26 | M. Rec |
| | 5HTR7 | P34969 | HTR7 | 3155 | No | 0.92 | 143 | 21 | M. Rec |
| | 5HTR2B | P41595 | HTR2B | 1833 | No | 0.92 | 208 | 26 | M. Rec |
| | 5HTR1A | P08908 | HTR1A | 214 | No | 0.92 | 420 | 161 | M. Rec |
| | 5HTR1B | P28222 | HTR1B | 1898 | Yes | 0.92 | 442 | 169 | M. Rec |
| | B2AR | P07550 | ADRB2 | 210 | No | 0.92 | 14 | 7 | M. Rec |
| | B1AR | P08588 | ADRB1 | 213 | No | 0.92 | 14 | 7 | M. Rec |
| | B3AR | P13945 | ADRB3 | 246 | Yes | 0.92 | 14 | 7 | M. Rec |
| | 5HTR1D | P28221 | HTR1D | 1983 | No | 0.92 | 179 | 127 | M. Rec |
| 019 | 5HTR2A | P28223 | HTR2A | 224 | No | 0.93 | 635 | 36 | M. Rec |
| | D(2)DR | P14416 | DRD2 | 217 | No | 0.92 | 1559 | 132 | M. Rec |
| | 5HTR2C | P28335 | HTR2C | 225 | No | 0.92 | 392 | 24 | M. Rec |
| | 5HTR7 | P34969 | HTR7 | 3155 | No | 0.92 | 228 | 19 | M. Rec |
| | 5HTR2B | P41595 | HTR2B | 1833 | No | 0.92 | 392 | 24 | M. Rec |
| | B2AR | P07550 | ADRB2 | 210 | No | 0.91 | 18 | 7 | M. Rec |
| | B1AR | P08588 | ADRB1 | 213 | No | 0.91 | 19 | 7 | M. Rec |
| | 5HTR1A | P08908 | HTR1A | 214 | No | 0.91 | 801 | 133 | M. Rec |
| | B3AR | P13945 | ADRB3 | 246 | Yes | 0.91 | 18 | 7 | M. Rec |
| | D(1A)DR | P21728 | DRD1 | 2056 | No | 0.91 | 194 | 20 | M. Rec |
| | D(4)DR | P21917 | DRD4 | 219 | No | 0.91 | 632 | 23 | M. Rec |
| | D(1B)DR | P21918 | DRD5 | 1850 | No | 0.91 | 160 | 20 | M. Rec |
| | 5HTR1D | P28221 | HTR1D | 1983 | No | 0.91 | 315 | 101 | M. Rec |
| | 5HTR1B | P28222 | HTR1B | 1898 | Yes | 0.91 | 841 | 141 | M. Rec |
| | HH1R | P35367 | HRH1 | 231 | No | 0.91 | 132 | 6 | M. Rec |

Synthetic Routes
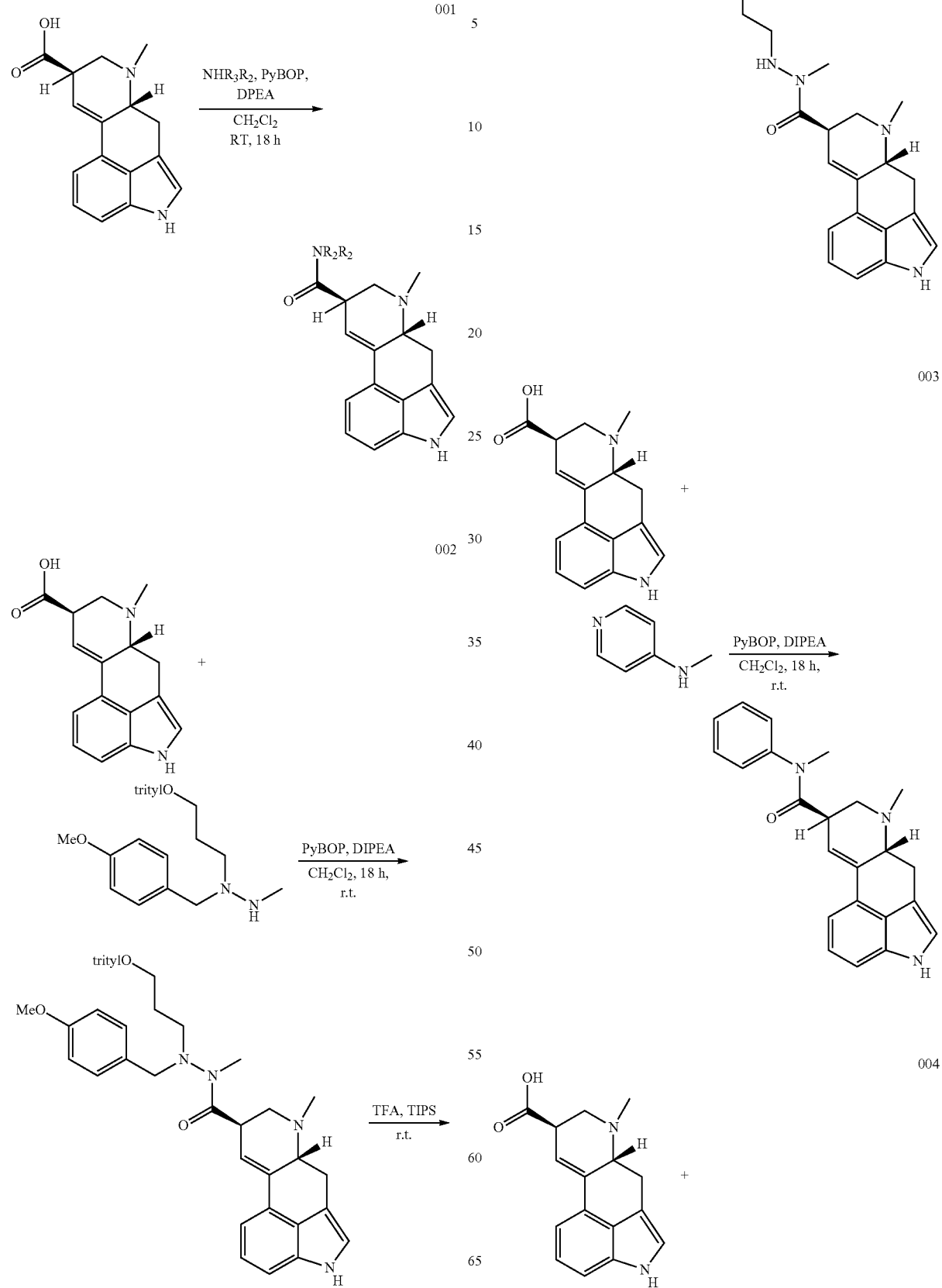

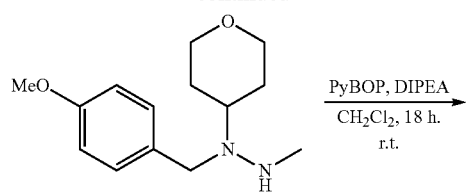
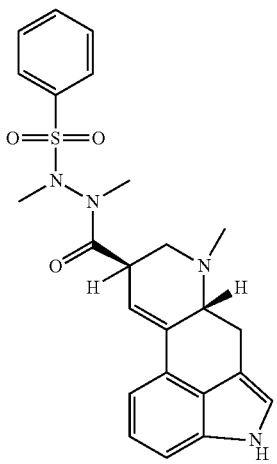
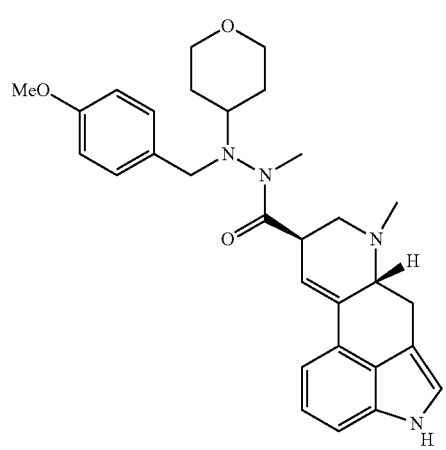
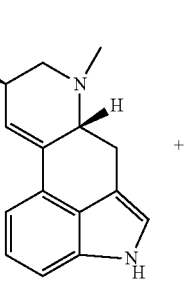
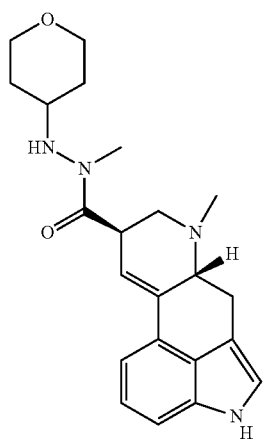
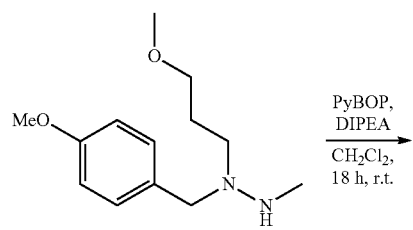
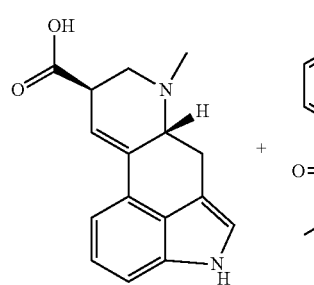
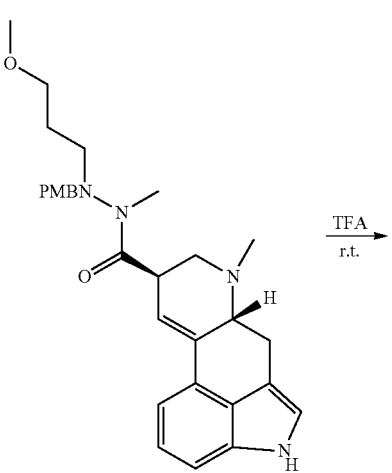

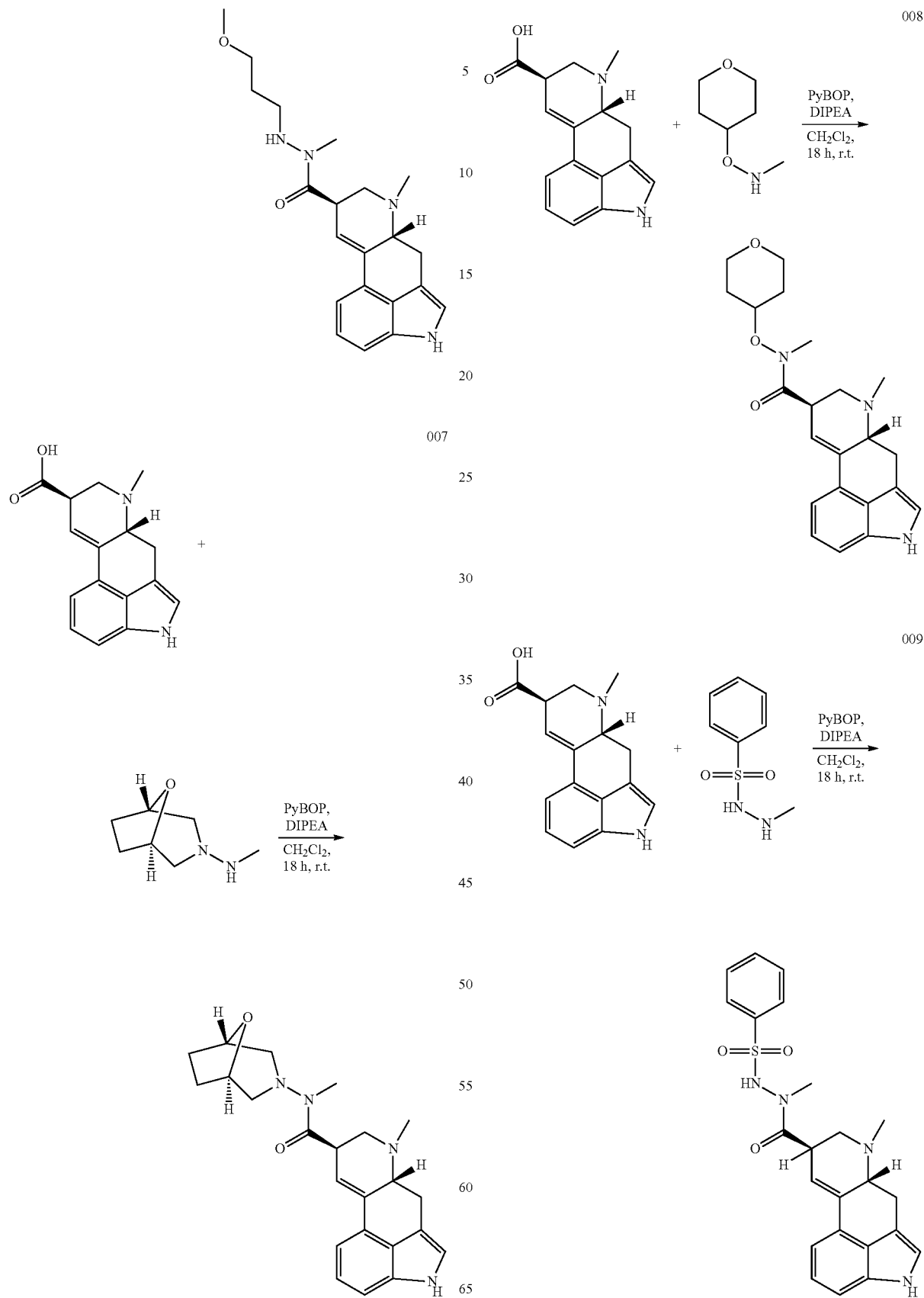

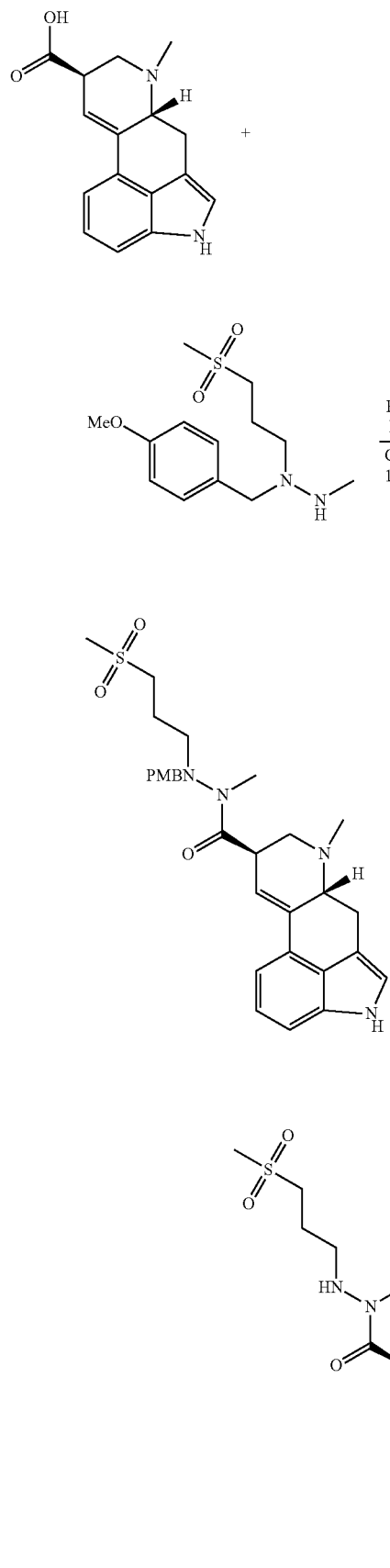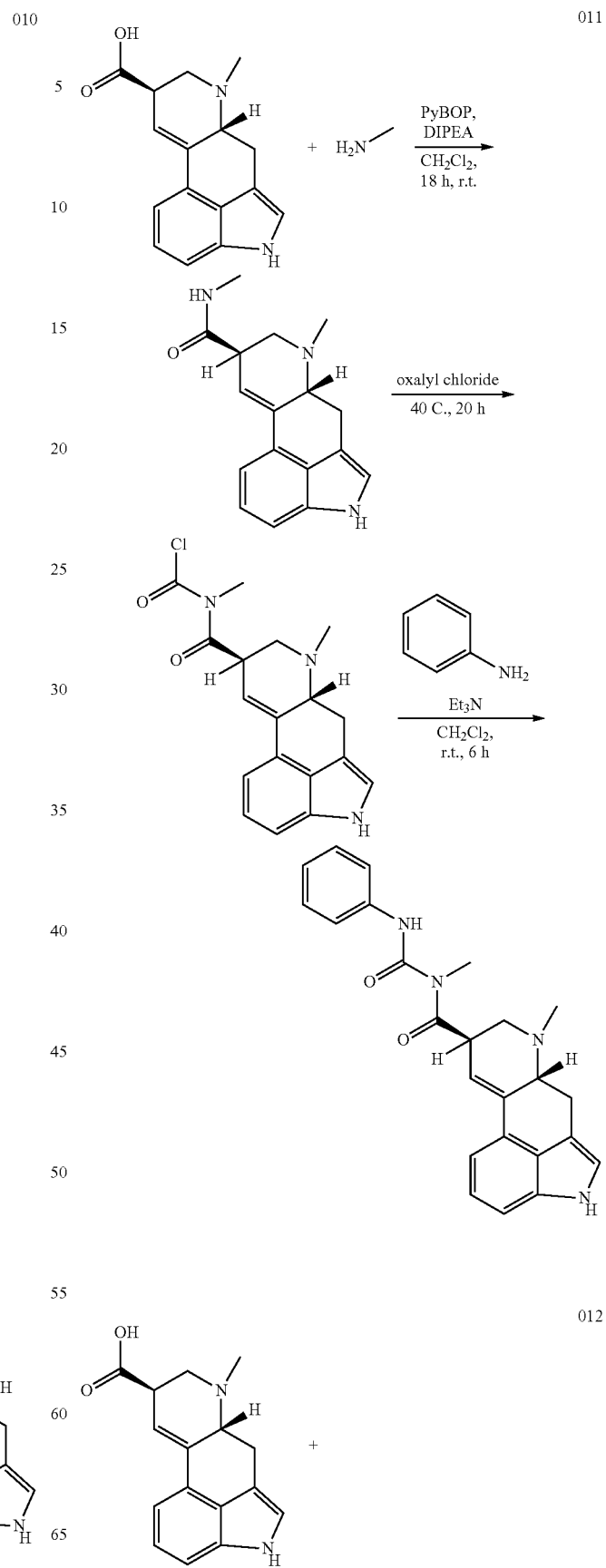

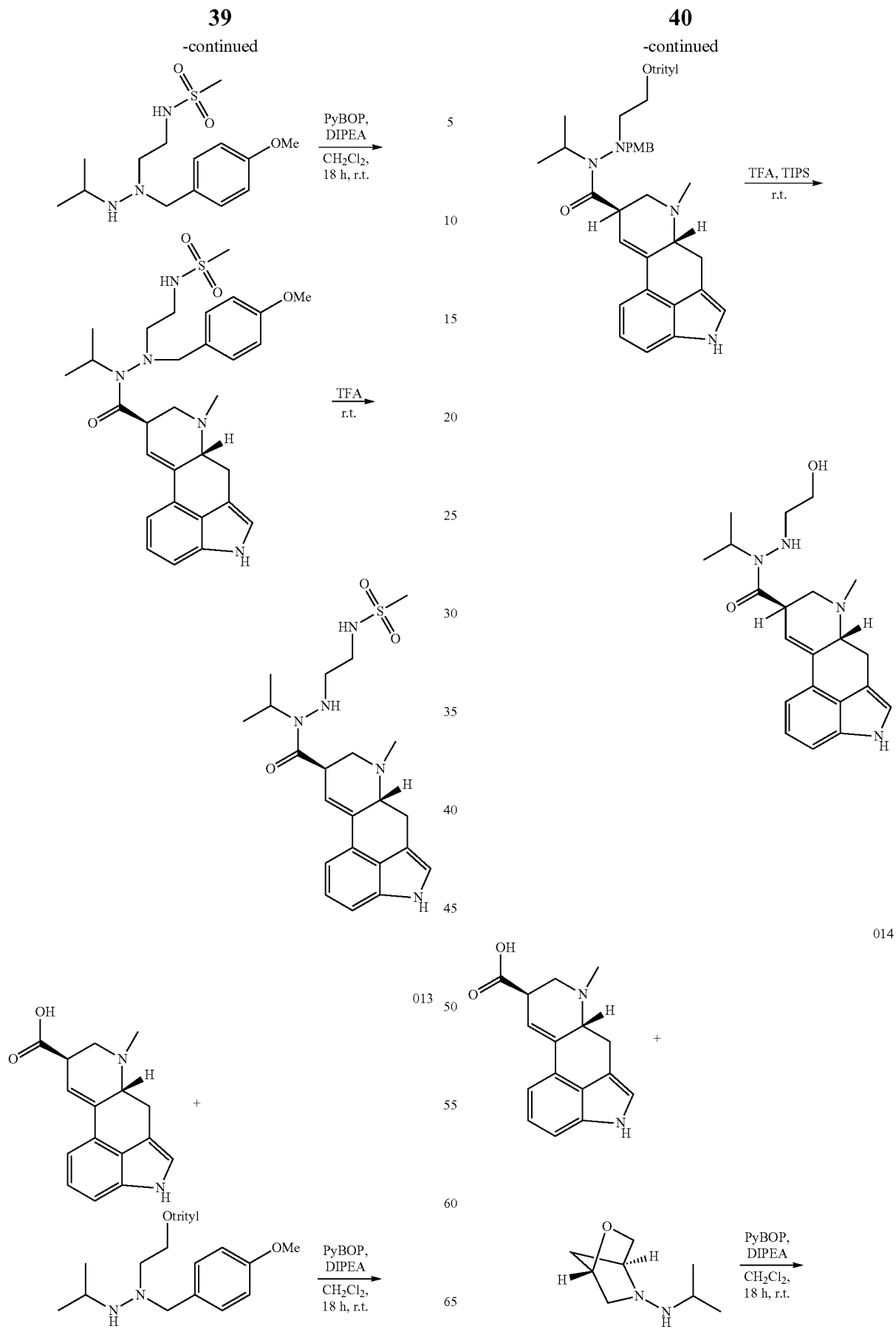

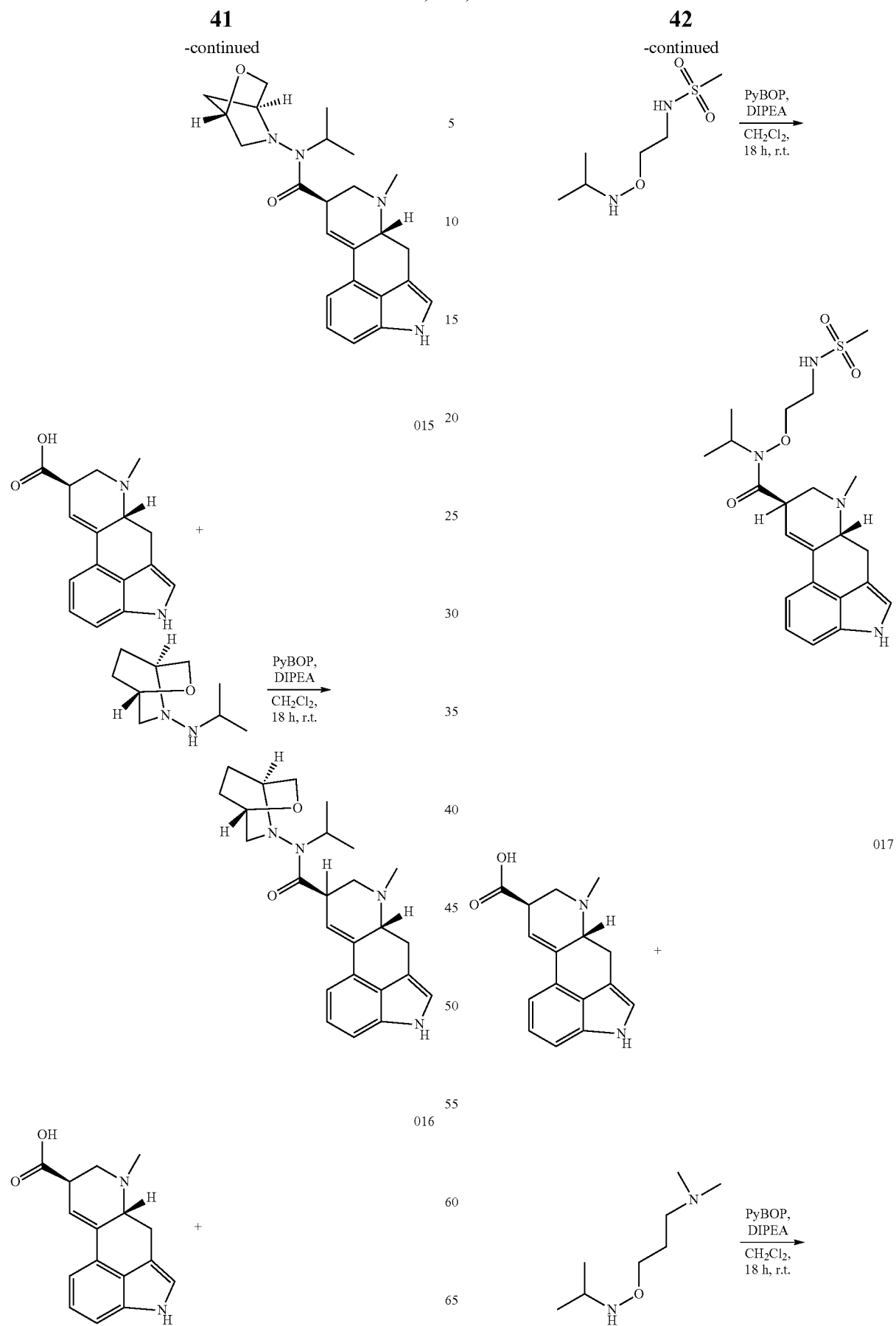

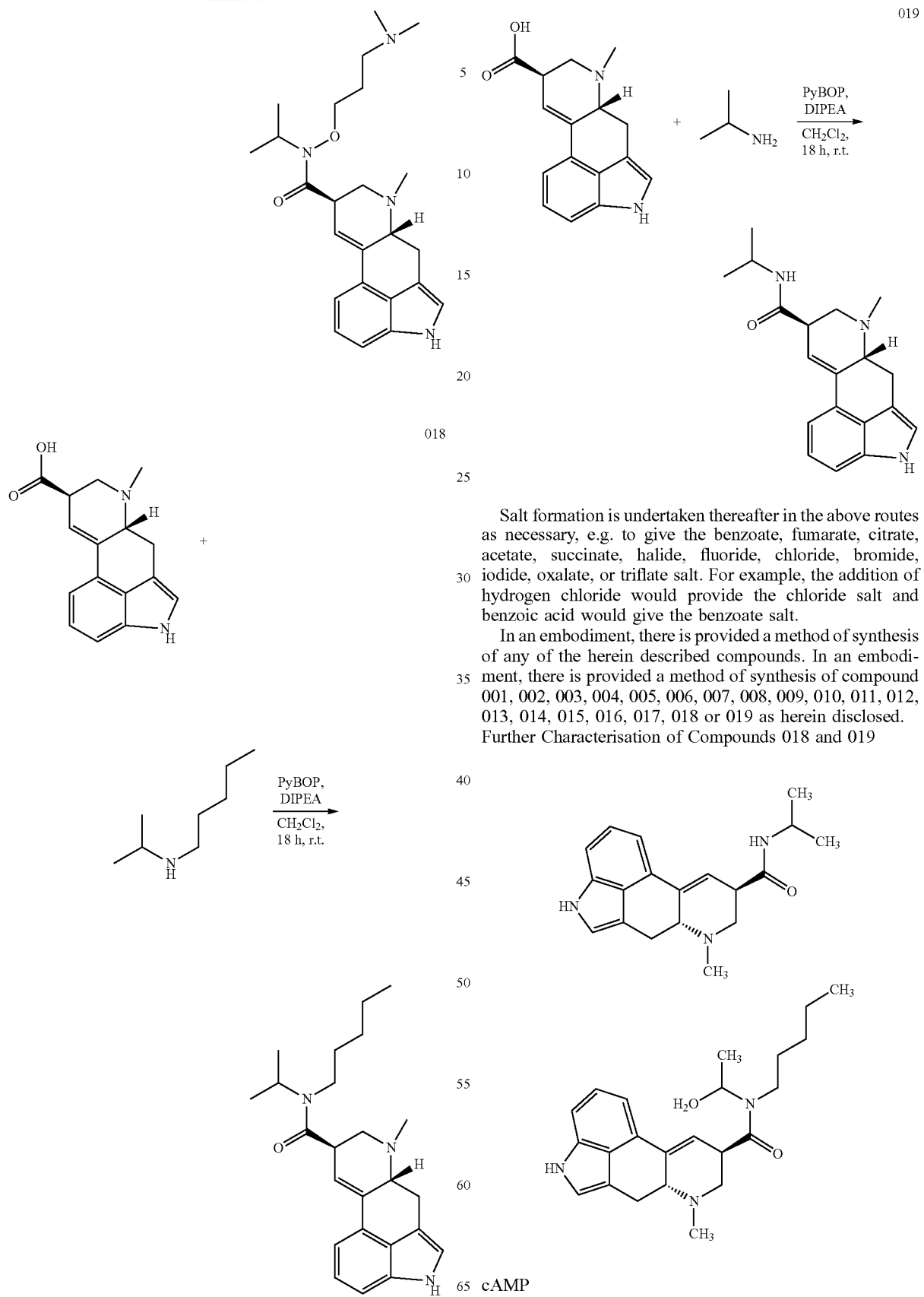

Salt formation is undertaken thereafter in the above routes as necessary, e.g. to give the benzoate, fumarate, citrate, acetate, succinate, halide, fluoride, chloride, bromide, iodide, oxalate, or triflate salt. For example, the addition of hydrogen chloride would provide the chloride salt and benzoic acid would give the benzoate salt.

In an embodiment, there is provided a method of synthesis of any of the herein described compounds. In an embodiment, there is provided a method of synthesis of compound 001, 002, 003, 004, 005, 006, 007, 008, 009, 010, 011, 012, 013, 014, 015, 016, 017, 018 or 019 as herein disclosed.

Further Characterisation of Compounds 018 and 019 cAMP

Compounds 018 (above, left) and 019 (above, right) were assayed using a serotonin (1a, 1b, 2a, 2c and 7 receptors)

cAMP assay, provided by Multispan. The reference used was 10 μM forskolin (a cAMP activator) to calculate the percentage relative response, serotonin was used as the control. The results can be seen in FIG. 1. Compound 019 was active against in all other receptor assays. The results indicate that compound 019 stimulates the $5HT_{2a}R$ leading to downstream activation of cAMP, although the curve response seems atypical compared to the serotonin control.

$IP_1$

Figure 2:
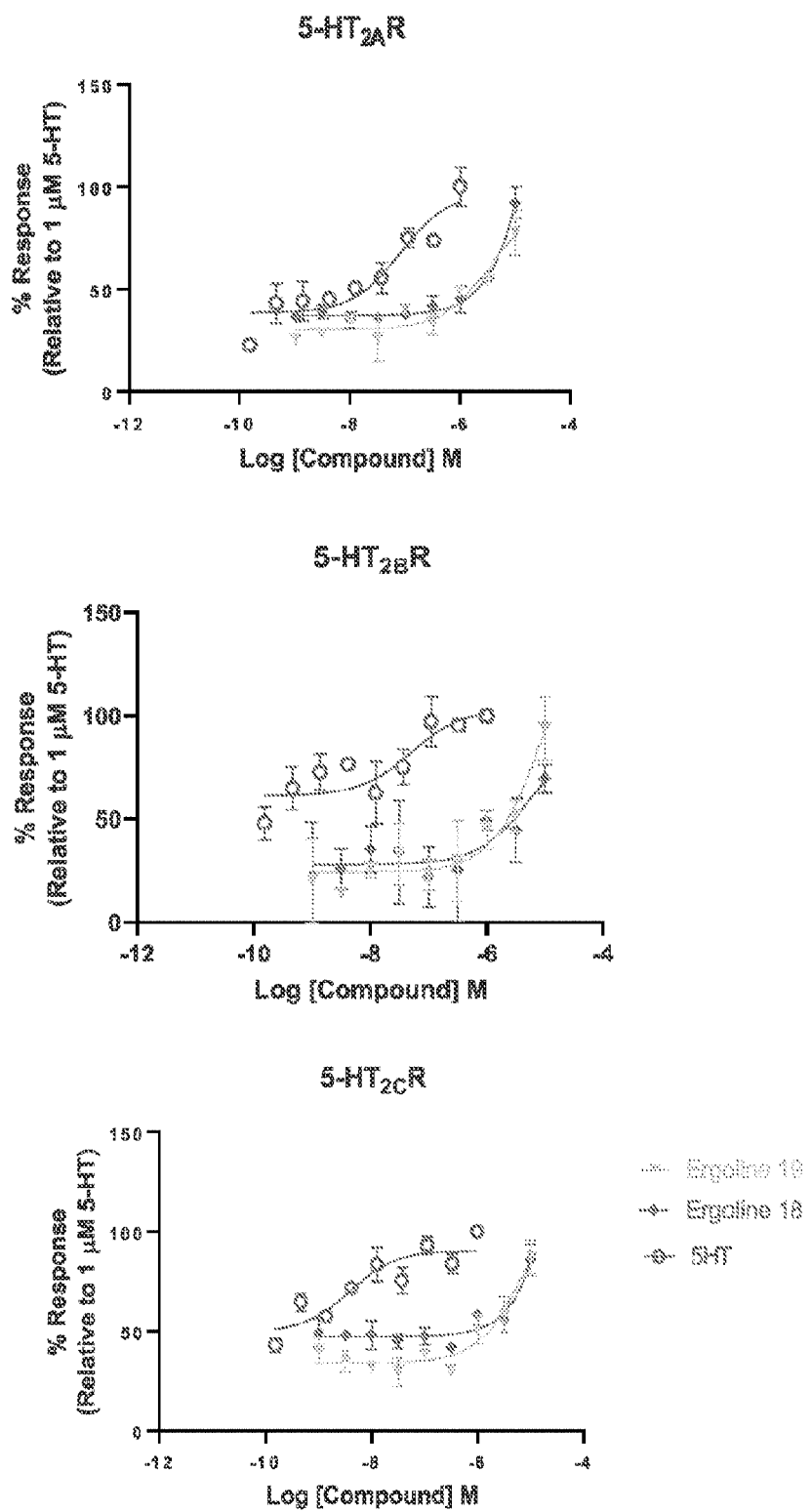
FIG. 2 shows serotonin (2a, 2b and 2c receptors) inositol phosphate 1 ($IP_1$) assay results for compounds 018 and 019.

Compounds 018 and 019 were assayed using a serotonin (2a, 2b and 2c receptors) inositol phosphate 1 ($IP_1$) assay, provided by Multispan. The reference used was 1 μM serotonin to calculate the percentage relative response. The results can be seen in FIG. 2. Both compounds appear to some activity against all three target receptors in this assay. This may imply that the compounds do not activate any $G\alpha_{q/11}$ pathway.

$Ca^{2+}$

Figure 3:
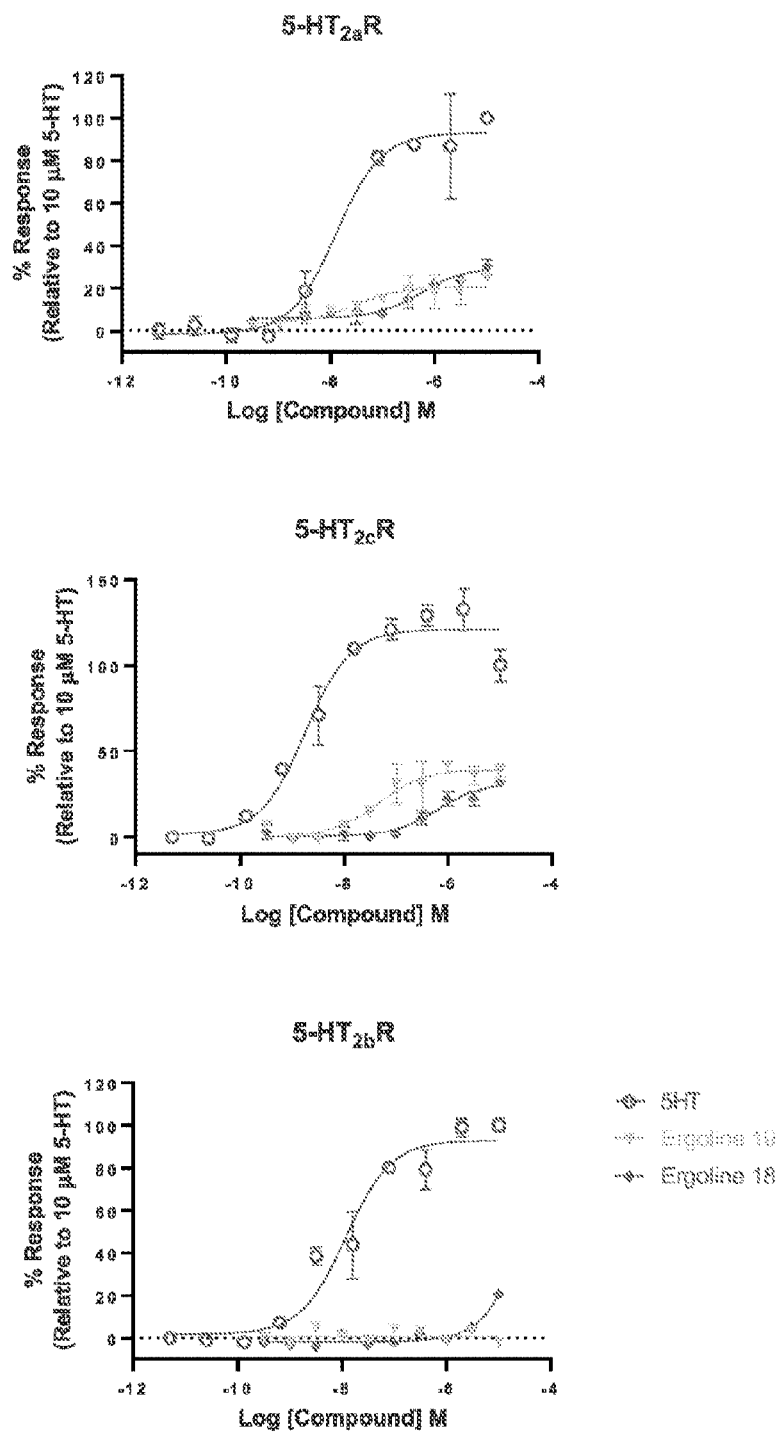
FIG. 3 shows serotonin (2a, 2b and 2c receptors) calcium ($Ca^{2+}$) assay results for compounds 018 and 019.

Compounds 018 and 019 were assayed using a serotonin (2a, 2b and 2c receptors) calcium ($Ca^{2+}$) assay, provided by Multispan. The reference used was 10 μM serotonin to calculate the percentage relative response in relative light units (RLU). The results can be seen in FIG. 3. Both compounds have some activity against the 2a and 2c receptors.

B-Arrestin

Figure 4:
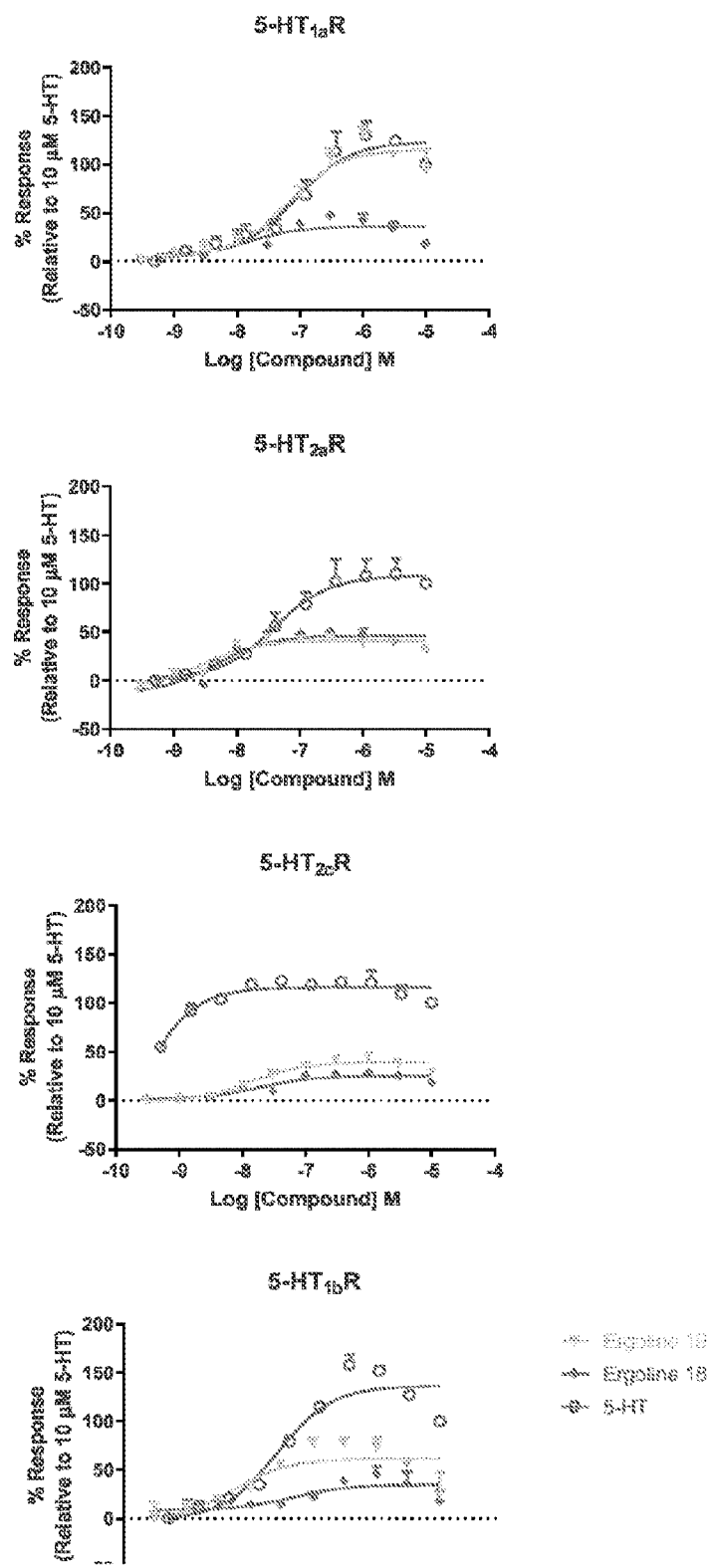
FIG. 4 shows serotonin (1a, 1b, 2a and 2c receptors) B-arrestin assay results for compounds 018 and 019.

Compounds 018 and 019 were assayed using a serotonin (1a, 1b, 2a and 2c receptors) B-arrestin assay, provided by DiscoverX. The reference used was 10 μM serotonin to calculate the percentage relative response. The results can be seen in FIG. 4. In general, both compounds exhibited some activity in comparison to serotonin.

Figure 5:
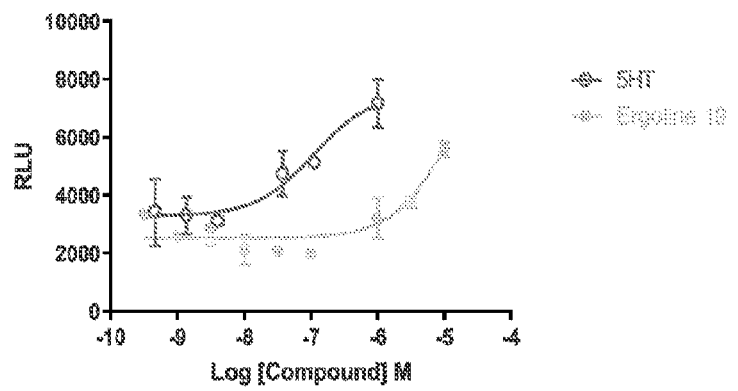
FIG. 5 shows serotonin 2b receptor B-arrestin assay results for compounds 018 and 019.
Figure 5:
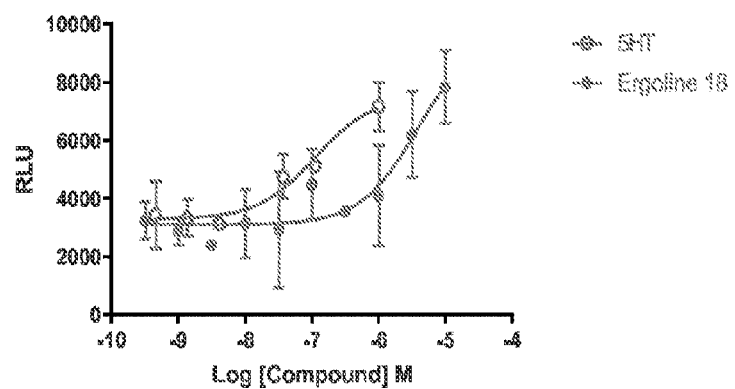

The compounds were also assayed in a serotonin 2b receptor B-arrestin assay, the results of which can be seen in FIG. 5.

Reagent Information

B-Arrestin:

| | |
|---|---|
| HTR1A PathHunter ® eXpress HTR1A CHO-K1 β-Arrestin GPCR Assay 200 dp (2 × 96-well) | 93-0696E2CP0M |
| HTR1B PathHunter ® eXpress HTR1B U2OS β-Arrestin GPCR Assay 200 dp (2 × 96-well) | 93-0697E3CP6M |
| HTR2A PathHunter ® eXpress HTR2A U2OS β-Arrestin GPCR Assay 200 dp (2 × 96-well) | 93-0401E3CP19M |
| HTR2C PathHunter ® eXpress HTR2C U2OS β-Arrestin GPCR Assay 200 dp (2 × 96-well) Multispan β-Arrestin assay with CHO-K1-5HT$_{2b}$R cells- Catalog C1350-1a | 93-0289E3CP3M |

Homogeneous Time Resolved Fluorescence (HTRF) and Calcium:

IP-One Gq kit—cisbio—cat. No. 62IPAPEB
cAMP Gs dynamic kit—cisbio—cat. No. 62AM4PEC
FLIPR calcium 6 assay explorer kit—VWR—cat. No. MLDVR8190

Cells Used in HTRF and Calcium Assays:

MULTISCREEN™ HEK293T Cell Line Stably Expressing Human 5-HT1A Receptor, Catalog DC1319a
MULTISCREEN™ HEK293T Cell Line Stably Expressing Human 5-HT1B Receptor, Catalog DC1320a
MULTISCREEN™ HEK293T Cell Line Stably Expressing Human 5HT1B Receptor, Catalog DC1320a
MULTISCREEN™ CHO-K1 Cell Line Stably Expressing Human 5-HT2A Receptor, Catalog DC1324-1
MULTISCREEN™ CHO-K1 Cell Line Stably Expressing Human 5-HT2B Receptor, Catalog DC1325-1
MULTISCREEN™ CHO-K1 Cell Line Stably Expressing Human 5-HT2C Receptor, Catalog DC1326-1
MULTISCREEN™ HEK293T Cell Line Stably Expressing Human 5-HT7 Receptor, Catalog DC1334

For the B-arrestin assays the cells came with the kits apart from the 2b receptor assay (Valiscreen serotonin 5HT-26 (human) cell line—ES-314-C, Perkin Elmer).

The invention claimed is:

1. A compound of Formula (I):

(I)

wherein X is methyl, Y is N($C_{1-6}$ alkyl) and Z is OH; or a pharmaceutically acceptable salt thereof.

2. The compound of claim 1, wherein X is methyl, Y is N($C_3$ alkyl) and Z is OH; or a pharmaceutically acceptable salt thereof.

3. A compound of Formula (I):

(I)

wherein X is methyl, Y is NH and Z is a $C_3$-$C_{10}$ heteroaromatic or heterocyclic group consisting of one, two or three heteroatoms independently selected from O and N; or a pharmaceutically acceptable salt thereof.

4. The compound of claim 3, wherein X is methyl, Y is NH and Z is a $C_3$-$C_{10}$ heterocyclic group consisting of one, two or three heteroatoms independently selected from O and N; or a pharmaceutically acceptable salt thereof.

5. The compound of claim 3, wherein X is methyl, Y is NH and Z is a $C_6$ heterocyclic group consisting of one, two or three heteroatoms independently selected from O and N; or a pharmaceutically acceptable salt thereof.

6. The compound of claim 3, wherein X is methyl, Y is NH and Z is a $C_6$ heterocyclic group consisting of one heteroatom independently selected from O and N; or a pharmaceutically acceptable salt thereof.

7. The compound of claim 3, wherein X is methyl, Y is NH and Z is a $C_6$ heterocyclic group consisting of one heteroatom which is O; or a pharmaceutically acceptable salt thereof.

8. A compound of Formula (I):

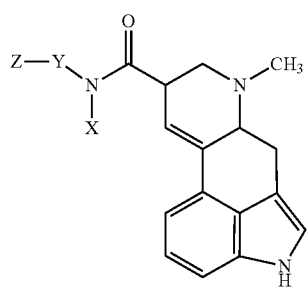

(I)

wherein X is methyl, Y is NH and Z is $SO_2$—$C_{6-10}$ aryl; or a pharmaceutically acceptable salt thereof.

9. The compound of claim 8, wherein X is methyl, Y is NH and Z is $SO_2$—$C_6$ aryl; or a pharmaceutically acceptable salt thereof.

10. A compound of Formula (I):

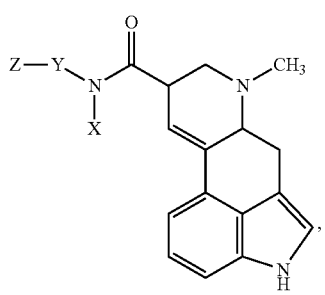

(I)

wherein X is isopropyl, Y is a bond and Z is $C_5$ alkyl; or a pharmaceutically acceptable salt thereof.

11. A compound of Formula (I):

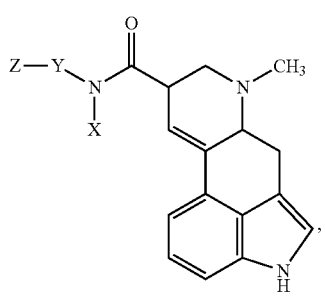

(I)

wherein X is isopropyl and Y—Z together form the group selected from: O—$(CH_2)_3$—$N(CH_3)_2$, NH—$(CH_2)_2$—OH, NH—$(CH_2)_3$—$OCH_3$, NH—$(CH_2)_2$—NH—$SO_2CH_3$, O—$(CH_2)_2$—NH—$SO_2CH_3$; or a pharmaceutically acceptable salt thereof.

12. The compound of claim 11, wherein X is isopropyl and Y—Z together form the group: NH—$(CH_2)_2$—OH; or a pharmaceutically acceptable salt thereof.

13. The compound of claim 11, wherein X is isopropyl and Y—Z together form the group: NH—$(CH_2)_3$—$OCH_3$; or a pharmaceutically acceptable salt thereof.

14. The compound of claim 11, wherein X is isopropyl and Y—Z together form the group: O—$(CH_2)_3$—$N(CH_3)_2$; or a pharmaceutically acceptable salt thereof.

15. A compound of Formula (I):

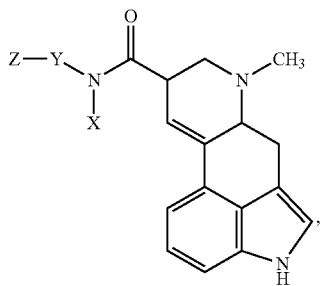

(I)

wherein X is methyl and Y—Z together form the group: NH—$(CH_2)_3$—$SO_2CH_3$; or a pharmaceutically acceptable salt thereof.

16. The compound of claim 11, wherein X is isopropyl and Y—Z together form the group: NH—$(CH_2)_2$—NH—$SO_2CH_3$; or a pharmaceutically acceptable salt thereof.

17. The compound of claim 11, wherein X is isopropyl and Y—Z together form the group: O—$(CH_2)_2$—NH—$SO_2CH_3$; or a pharmaceutically acceptable salt thereof.

18. A compound of Formula (I):

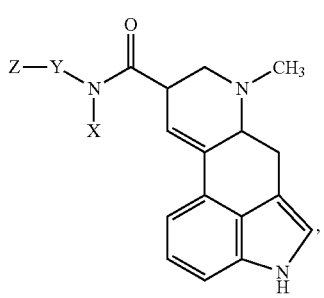

(I)

wherein X is isopropyl or methyl and Y—Z together form the group: NH-phenyl, pyridine, O-morpholine, NH-morpholine, NH—$SO_2$-Phenyl, $NCH_3$—$SO_2$-Phenyl, CONH-Phenyl, 8-oxa-3-azabicyclo[3.2.1]octane or 2-oxa-5-azabicyclo[2.2.1]heptane; or a pharmaceutically acceptable salt thereof.

19. A method of treatment of a subject, comprising administering a compound of claim 10, or pharmaceutically acceptable salt thereof to the subject, wherein the subject has depression, anxiety or a pain condition.

20. A method of treatment of a subject, comprising administering the compound of claim 9 or pharmaceutically acceptable salt thereof to the subject, wherein the subject has depression, anxiety or a pain condition.

* * * * *